US005658563A

United States Patent [19]
Krapcho et al.

[11] Patent Number: 5,658,563
[45] Date of Patent: Aug. 19, 1997

[54] INSECTICIDALLY EFFECTIVE PEPTIDES

[75] Inventors: Karen J. Krapcho; J. R. Hunter Jackson; Bradford Carr VanWagenen; Robert Marden Kral, Jr., all of Salt Lake City, Utah

[73] Assignees: FMC Corporation, Philadelphia, Pa.; NPS Pharmaceuticals, Inc., Salt Lake City, Utah

[21] Appl. No.: 463,212

[22] Filed: Jun. 5, 1995

Related U.S. Application Data

[60] Division of Ser. No. 215,084, Mar. 18, 1994, Pat. No. 5,461,032, which is a continuation-in-part of Ser. No. 859,925, Mar. 24, 1992, abandoned, which is a continuation-in-part of Ser. No. 662,373, Mar. 1, 1991, abandoned.

[51] Int. Cl.$^6$ ............................ C12N 15/63; A61K 48/00
[52] U.S. Cl. .................. 424/93.2; 435/320.1; 435/172.3
[58] Field of Search ..................... 424/93.2; 435/320.1, 435/172.3

[56] References Cited

U.S. PATENT DOCUMENTS

| | | | |
|---|---|---|---|
| 4,683,195 | 7/1987 | Mullis et al. | 435/91.2 |
| 4,683,202 | 7/1987 | Mullis | 435/6 |
| 4,703,008 | 10/1987 | Lin | 435/240.2 |
| 4,797,279 | 1/1989 | Karamata et al. | 424/93 R |
| 4,855,405 | 8/1989 | Yoshioka et al. | 530/300 |
| 4,861,595 | 8/1989 | Barnes et al. | 424/195.1 |
| 4,879,236 | 11/1989 | Smith et al. | 435/320.1 |
| 4,918,107 | 4/1990 | Nakajima et al. | 514/616 |
| 4,925,664 | 5/1990 | Jackson et al. | 424/537 |

FOREIGN PATENT DOCUMENTS

| | | |
|---|---|---|
| 2005658 | 6/1990 | Canada . |
| 0 325 400 A1 | 1/1989 | European Pat. Off. . |
| 0 340 948 | 4/1989 | European Pat. Off. . |
| 0 374 940 | 6/1990 | European Pat. Off. . |
| 0 395 357 | 10/1990 | European Pat. Off. . |
| 0 431 829 | 6/1991 | European Pat. Off. . |
| 0 505 207 | 9/1992 | European Pat. Off. . |
| WO89/07608 | 8/1989 | WIPO . |
| WO92/16637 | 10/1992 | WIPO . |
| WO93/23428 | 11/1993 | WIPO . |

OTHER PUBLICATIONS

Adams, et al., "Isolation and Biological Activity of Synaptic Toxins from the Venom of The Funnel Web Spider, *Agelenopsis aperta*", in Insect Neurochemistry and Neurophysiology 1986, Borkevec and Gelman, eds., Humana Press, New Jersey, 1986.

Carbonell, et al., "Synthesis of a gene coding for an insect-specific scorpion neurotoxin and attempts to express it using baculovirus vectors", *Gene*, 73:409–418 (1988).

Chomczynski, et al., "Single–Step Method of RNA Isolation by Acid Guanidinium Thiocyanate–Phenol–Chloroform Extraction", *Analytical Biochemistry*, 162:156–159 (1987).

Cutler, et al., "Electroporation: Being Developed to Transform Crops, (success with model crop confirmed)", *AG Biotech. News*, 7(5):3 & 17 (1990).

Davies, et al., "Recombinant baculovirus vectors expressing gluthathione–S–transferase fusion proteins", *Biotech.*, 11:933–936 (1993).

Dunwiddie, T.V., "The Use of In Vitro Brain Slices in Neuropharmacology", *Electrophysiological Techniques in Pharmacology*, H.M. Geller, 25ed. Alan R. Liss, Inc., New York, pp. 65–90 (1986).

Fuqua, et al., "A simple PCR Method for detection and cloning low abundant transcript", *Biotechniques*, 9:206–211 (1990).

Hink, et al., "Expression of three recombinant proteins using baculovirus vectors in 23 insect cell lines", *Biotechnol. Prog.*, 7:9–14 (1991).

Jackson and Parks "Spider Toxins: Recent Applications in Neurobiology", *Ann Rev Neurosci.*, 12:405–414 (1989).

Jones, et al., "Molecular Cloning Regulation and Complete Sequence of a Hemocyanin–Related Juvenile Hormone–Suppressible Protein From Insect Hemolymphs", *J. Biol. Chem.*, 265:8596 (1990).

Miller, et al., "Bacterial, Viral and Fungal Insecticides", *Science*, 219:715–721 (1983).

Rossi, et al., "An Alternate Method for Synthesis of Double–Stranded DNA Segments", *J. Biol. Chem.*, 257:9226 (1982).

Saiki, et al., "Primer–Directed Enzymatic Amplification of DNA with a Thermostable DNA Polymerase", *Science*, 239:487–491, 1988.

Sambrook, et al., "Molecular Cloning a Laboratory Manual", Second Ed., Cold Spring Harbor Press (1989).

Scopes, "Measurement of Protein by Spectrophotometry at 205 nm", *Anal. Biochem.*, 59:277–282, 1974.

Skinner, et al., "Purification and characterization of two classes of neurotoxins from the funnel web spider, *Agelenopsis aperta*", *J. Biol. Chem.*, 264:2150–2155 (1989).

Stapleton, et al., "Curtatoxins, neurotoxic insecticidal polypeptides isolated from the funnel web spider *Hololena curta*", *J. Biol. Chem.* 265:2054–2059 (1990).

Stewart, et al., "Construction of an improved baculovirus insecticide containing an insect-specific toxin gene", *Nature*, 352:85–88 (1991).

Summers and Smith, "A Manual of Methods for Baculovirus Vectors and Insect Cell Culture Procedures", *Texas Agricultural Experiment Bulletin*, No. 1555, 1, 1988.

Tomalski and Miller, "Insect paralysis by baculovirus–mediated expression of a mite neurotoxin gene", *Nature*, 352:82–85 (1991).

Vialard, et al., "Synthesis of the Membrane Fusion and Hemagglutinin Proteins of Measles Virus, Using a Novel Baculovirus Vector Containing the β–Galactosidase Gene", *J. Virology*, 64:37–50 (1990).

(List continued on next page.)

*Primary Examiner*—Che S. Chereskin
*Attorney, Agent, or Firm*—Woodcock Washburn Kurtz Mackiewicz & Norris

[57] ABSTRACT

The invention provides insecticidally effective peptides isolatable from Diguetia spider venom, methods for preparing and using insecticides, and DNA encoding such insecticidally effective peptides.

10 Claims, 8 Drawing Sheets

OTHER PUBLICATIONS

Waddel and Hill, "A Simple Ultraviolet Spectrophotometric Method for the Determination of Protein", *J. Lab. Clin. Med.* 48:311–314 (1956).

Zlotkin, et al., "An Excitatory and a Depressant Insect Toxin from Scorpion Venom both Affect Sodium Conductance and Possess a Common Binding Site", *Arch. Biochem. and Biophysics*, 240:877–887 (1985).

McCutchen, et al., "Development of a Recombinant Baculovirus Expressing an Insect–Selective Neurotoxin: Potential for Pest Control", *Biotechnology*, 9:848–852, 1991.

Bentzien, "Biology of the Spider *Diguetia imperiosa*", *The Pan–Pacific Entomologist*, 49:110–123, 1973.

Quicke, et al., "Extended summaries Pesticides Group and Physicochemical and Biophysical Panel Symposium Novel Approaches in Agrochemical Research", *Pestic. Sci.*, 20:315–317, 1987.

Quistad, et al., "Insecticidal Activity of Spider (Araneae), Centipede (Chilopoda), Scorpion (Scorpionida), and Snake (Serpentes) Venoms", *J. Econ. Entom.*, 85:33–39, 1992.

Nentwig, et al. "Comparative Investigations on the Effect of the Venoms of 18 Spider Species onto the Cockroach *Blatta orientalis* (Blattodea)", *Zool. Jb. Physiol.* 96:279–290 (1992).

Friedel, et al., "Immobilizing and Lethal Effects of Spider Venoms on the Cockroach and the Common Mealbeetle", *Toxicon*, 27:305–316, 1989.

Gertsch, "American Spiders", Van Nostrand Reinhold, NY, pp. 215–216, 1979.

Roth, "The Spider Genus Tegenaria in the Western Hemisphere (Agelenidae)", *Amer. Museum Novitates*, 2323:1–33, 1968.

Vest, "Necrotic Arachnidism in the Northwest United States and Its Probably Relationship to *Tegenaria agrestis* (Walckenaer) Spiders", *Toxicon*, 25:175–184, 1987.

Creighton, "Modification of the Amino and Carboxyl Terminal Groups", *Proteins: Structure and Molecular Properties*, W.H. Freeman and Company: New York, pg. 75–76, 1983.

Blobel, "Intracellular Protein Topogenesis", *Proc. Natl. Acad. Sci. USA*, 77:1496–1500, 1980.

Frohman, "RACE: Rapid amplification of cDNA ends", in *PCR Protocols*, Innis, et al., eds. Academic Press, San Diego, CA, pp. 28–38, 1990.

Raineri, et al., "Agrobacterium–Mediated Transformation of Rice (Oryza Sativa L.)", *Biotechnology*, 8:33–38, 1990.

Fromm, et al., "Inheritance and Expression of Chimeric Genes in the Progeny of Transgenic Maize Plants", *Biotechnology*, 8:833–839, 1990.

Harlow, et al., "*Antibodies: A Laboratory Manual*", Cold Spring Harbor Press: New York, 1988.

Smith, et al. "$M_r$ 26,000 antigen of *Schistosoma japonicum* recognized by resistant WEHI 129/J mice is a parasite gluthathione S–transferase", *Proc. Natl. Acad. Sci. USA*, 83:8703–8707, 1986.

Raymond, "Presentation d'un programme Basic d'analyse log–probit pour micro–ordinateur", *Set. Ent. med et Parasitol.*, 23:117–121 1985.

Luria, et al., *In General Virology*, John Wiley and Sons: New York, Chapter 2, pp. 21–32, 1978.

Kuroda, et al., "Synthesis of Biologically Active Influenza Virus Hemagglutinin in Insect Larvae", *J. of Virology*, 63:1677–1685, 1989.

Wood, "Protease Degradation of *Autographa californica* Nuclear Polyhedrosis Virus Proteins", *Virology*, 103:392–399, 1980.

Price, et al., "Complementation of recombinant baculoviruses by coinfection with wild–type facilities production insect larvau of antigenic proteins of hepatitis B virus and influenza virus", *Proc. Natl. Acad. Sci. USA*, 86:1453–1456, 1989.

Bers, et al., "Protein and Nucleic Acid Blotting and Immunobiochemical Detection", *BioTechniques*, 3:276–288, 1985.

Bronstein, et al., "Rapid and Sensitive Detection of DNA in Southern with Chemiluminescence", *BioTechniques*, 8:310–314, 1990.

Quistad, et al., "Paralytic and Insecticidal Toxins from the Funnel Web Spider, *Hololena curta*", *Toxicon*, 29:329–336, 1991.

Bowers, et al., "Identification and purification of an irreversible presynaptic neurotoxin from the venom of spider *Hololena curta*", *Proc. Natl. Acad. Sci. USA*, 84:3506–3510, 1987.

Geren, "Neurotoxins and Necrotoxins of Spider Venoms", *J. Toxicol. –Toxin Reviews*, 5:161–170, 1986.

Grishin, "Toxin components from *Buthus eupeus* and *Lycosa singoriensis* venoms", *Shemyakin Institute of Bioorganic Chemistry*, USSR Academy of Science, Moscow 117988, GSP–1, USSR.

Hermann and Frischauf, "Isolation of Genomic DNA", *Methods in Enzymology*, 152:180–183, 1987.

Kaneda, et al., "Scorpion toxin prolongs an inactivation phase of the voltage–dependent sodium current in rat isolated single hippocampal neurons", *Brain Res.*, 487–192–195, 1989.

McKnight, et al., "Transcriptional Control Signals of an Eucaryotic Protein–Coding Gene", *Science*, 217:316, 1982.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 56 amino acids
        ( B ) TYPE: amino acid
        ( D ) TOPOLOGY: unknown ( x i ) SEQUENCE DESCRIPTION: SEQ ID NO:1:

```
Ala  Lys  Asp  Gly  Asp  Val  Glu  Gly  Pro  Ala  Gly  Cys  Lys  Lys  Tyr
                     5                        10                       15

Asp  Val  Glu  Cys  Asp  Ser  Gly  Glu  Cys  Cys  Xaa  Lys  Gln  Tyr  Leu
                    20                        25                       30

Trp  Tyr  Lys  Trp  Arg  Pro  Leu  Asp  Cys  Arg  Cys  Leu  Lys  Ser  Gly
                    35                        40                       45

Phe  Phe  Ser  Ser  Lys  Cys  Val  Cys  Arg  Asp  Val
                    50                        55
```

( 2 ) INFORMATION FOR SEQ ID NO:2:

( i ) SEQUENCE CHARACTERISTICS:
        ( A ) LENGTH: 275 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
GCC  AAG  GAC  GGC  GAC  GTC  GAG  GGG  CCT  GCG  GGC  TGC  AAG  AAA        42
Ala  Lys  Asp  Gly  Asp  Val  Glu  Gly  Pro  Ala  Gly  Cys  Lys  Lys
1                    5                        10

TAC  GAC  GTA  GAG  TGC  GAC  AGT  GGA  GAG  TGC  TGC  MMS  AAG  CAG        84
Tyr  Asp  Val  Glu  Cys  Asp  Ser  Gly  Glu  Cys  Cys  Xaa  Lys  Gln
15                            20                       25
```

```
TAC CTG TGG TAC AAG TGG CGA CCC CTG GAT TGC CGA TGC CTA         126
Tyr Leu Trp Tyr Lys Trp Arg Pro Leu Asp Cys Arg Cys Leu
    30                  35                  40

AAG AGC GGT TTC TTC AGC AGC AAG TGC GTT TGC AGA GAC GTG         168
Lys Ser Gly Phe Phe Ser Ser Lys Cys Val Cys Arg Asp Val
        45                  50                  55

TAGATTTGAA ATGAAATTCG TGTTCTTTTT TGGTTGTAGA TGACCTAATG          218

AACAACTGA CATGAATAAA ACAAAATTGA ATGAATTGAA AAAAAAAAA            268

AAAAAGC                                                        275
```

( 2 ) INFORMATION FOR SEQ ID NO:3:

( i ) SEQUENCE CHARACTERISTICS:
        ( A ) LENGTH: 58 amino acids
        ( B ) TYPE: amino acid
        ( D ) TOPOLOGY: unknown ( x i ) SEQUENCE DESCRIPTION: SEQ ID NO:3:

```
Ala Lys Asp Gly Asp Val Lys Gly Pro Ala Gly Cys Met Lys Tyr
1               5                   10                  15

Lys Ser Gly Asp Cys Arg Gly Lys Thr Cys Cys Asp Gln Gln Tyr
                20                  25                  30

Leu Trp Tyr Lys Trp Arg Asn Leu Ala Cys Arg Cys Phe Thr Val
                35                  40                  45

Glu Val Phe Lys Lys Asp Cys Trp Cys Asn Asp Ile Ser
                50                  55
```

( 2 ) INFORMATION FOR SEQ ID NO:4:

( i ) SEQUENCE CHARACTERISTICS:
        ( A ) LENGTH: 204 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

```
GCC AAG GAT GGC GAT GTC AAG GGA CCT GCT GGC TGC ATG AAG          42
Ala Lys Asp Gly Asp Val Lys Gly Pro Ala Gly Cys Met Lys
1               5                   10

TAC AAG AGC GGA GAC TGC AGA GGC AAA ACT TGC TGC GAC CAA          84
Tyr Lys Ser Gly Asp Cys Arg Gly Lys Thr Cys Cys Asp Gln
15                  20                  25

CAG TAC CTC TGG TAC AAG TGG CGG AAT CTT GCA TGC AGG TGC         126
Gln Tyr Leu Trp Tyr Lys Trp Arg Asn Leu Ala Cys Arg Cys
    30                  35                  40

TTC ACG GTC GAA GTG TTC AAG AAG GAC TGC TGG TGC AAC GAC         168
Phe Thr Val Glu Val Phe Lys Lys Asp Cys Trp Cys Asn Asp
        45                  50                  55

ATC AGT TAATTCCACA TGAAGAAGTA AGCATCTCCT                        204
Ile Ser
```

( 2 ) INFORMATION FOR SEQ ID NO:5:

( i ) SEQUENCE CHARACTERISTICS:
        ( A ) LENGTH: 62 amino acids
        ( B ) TYPE: amino acid
        ( D ) TOPOLOGY: unknown ( x i ) SEQUENCE DESCRIPTION: SEQ ID NO:5:

```
Ala Lys Asp Gly Asp Phe Glu Gly Pro Pro Gly Xaa Leu Lys Met
1               5                   10                  15
```

```
Gly Glu Leu Xaa Lys Gly Gly Thr Xaa Xaa Thr Lys Val Tyr Lys
            20              25              30

Tyr Trp Lys Trp Arg Lys Leu Glu Cys Leu Gly Lys Asn Asp Gly
                35              40              45

Trp Phe Lys Lys Lys Phe Ile Cys Asp Glu Arg Xaa Asn Pro Xaa
                50              55              60

Xaa Xaa
```

( 2 ) INFORMATION FOR SEQ ID NO:6:

( i ) SEQUENCE CHARACTERISTICS:
        ( A ) LENGTH: 429 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:6:

```
ATATTACAAG CCGCTCCAGT AGCCGAAGAA GCCTAAGCCA AGAACCCAGG           50

TCCGCCACA ATG AAG GTT TTT GTT GTA CTG TTG TGC TTG TCT            92
          Met Lys Val Phe Val Val Leu Leu Cys Leu Ser
              -35                     -30

CTG GCA GCA GTT TAC GCC TTG GAG GAA AGA CTA GAC AAA GAC         134
Leu Ala Ala Val Tyr Ala Leu Glu Glu Arg Leu Asp Lys Asp
    -25                 -20                 -15

GCC GAC ATC ATG CTT GAT TCA CCA GCC GAC ATG GAA AGA GCG         176
Ala Asp Ile Met Leu Asp Ser Pro Ala Asp Met Glu Arg Ala
        -10                 -5                       1

AAG GAC GGT GAC GTG GAA GGG CCT GCG GGC TGC AAG AAA TAC         218
Lys Asp Gly Asp Val Glu Gly Pro Ala Gly Cys Lys Lys Tyr
            5               10                  15

GAC GTA GAG TGC GAC AGT GGA GAG TGC TGC MMS AAG CAG TAC         260
Asp Val Glu Cys Asp Ser Gly Glu Cys Cys Xaa Lys Gln Tyr
                20                  25

CTG TGG TAC AAG TGG CGA CCC CTG GAT TGC CGA TGC CTA AAG         302
Leu Trp Tyr Lys Trp Arg Pro Leu Asp Cys Arg Cys Leu Lys
30                      35                  40

AGC GGT TTC TTC AGC AGC AAG TGC GTT TGC AGA GAC GTG             341
Ser Gly Phe Phe Ser Ser Lys Cys Val Cys Arg Asp Val
    45                  50                  55

TAGATTTGAA AATGAAATTC GTGTTCTTTT TTGGTTGTAG ATGACCTAAT          391

GAAACAACTG ACATGAATAA AACAAAATTG AATGAATT                       429
```

( 2 ) INFORMATION FOR SEQ ID NO:7:

( i ) SEQUENCE CHARACTERISTICS:
        ( A ) LENGTH: 38 amino acids
        ( B ) TYPE: amino acid
        ( D ) TOPOLOGY: unknown ( x i ) SEQUENCE DESCRIPTION: SEQ ID NO:7:

```
Met Lys Val Phe Val Val Leu Leu Cys Leu Ser Leu Ala Ala
        -35                 -30                 -25

Val Tyr Ala Leu Glu Glu Arg Leu Asp Lys Asp Ala Asp Ile
            -20                 -15

Met Leu Asp Ser Pro Ala Asp Met Glu Arg
-10             -5                  -1
```

( 2 ) INFORMATION FOR SEQ ID NO:8:

( i ) SEQUENCE CHARACTERISTICS:
        ( A ) LENGTH: 421 base pairs ( B ) TYPE: nucleic acid
( C ) STRANDEDNESS: double
( D ) TOPOLOGY: linear ( x i ) SEQUENCE DESCRIPTION: SEQ ID NO:8:

| TTTAGCAGCC | CAAGGCTACA | GAGCTGCCGC | ACAGGTAAAC | CTGAACTACA | 50 |
| CAATGCCCCA | TGCCCACGCT | CAAACCACAT | ACACTCTTTC | CCCAACTTTT | 100 |
| TTTTGGTAA | AGACAGTTGT | TGCATTCTAA | AAGCACGTTT | TACTGCAGCT | 150 |
| GCTCAGACTG | TCTGCTGCTG | GTCGAGGCAG | AGTATGTTTC | CTACAGAATT | 200 |
| CCACCGAAGC | ATTGTTCGTG | GTACGACGCA | GTAAGCATGA | CGCTCAGTTT | 250 |
| TTTTTGAATC | GGAATATGTA | ATATCTGCAG | CGACACTTAT | TGAAATGTTT | 300 |
| CTCCTTCGAC | AAGCAATCGC | TTTATCGGAA | TACCTGCATG | ACATAACTGA | 350 |
| CAAAACACAT | GTGGCTCCAG | AAACAACGAA | AACATTCATT | CCTGTATATA | 400 |
| AGTATCGGAG | GAGTGCTGTA | T | | | 421 |

INSECTICIDALLY EFFECTIVE PEPTIDES

CROSS REFERENCE TO RELATED APPLICATIONS

This is a division of application Ser. No. 08/215,084, filed Mar. 18, 1994 now U.S. Pat. No. 5,461,032, which is a continuation-in-part of application Ser. No. 859,925, filed Mar. 24, 1992, now abandoned which is a continuation-in-part of application Ser. No. 662,373, filed Mar. 1, 1991, now abandoned.

FIELD OF THE INVENTION

This invention relates to insecticidally effective peptides. More particularly, the invention relates, inter alia, to insecticidally effective peptides isolatable from Diguetia spider venom, DNA encoding such insecticidally effective peptides, methods for producing said peptides, and methods for controlling invertebrate pests.

BACKGROUND OF THE INVENTION

In recent years, the public has become acutely aware of the environmental hazards and mammalian toxicity associated with the use of synthetic insecticides. As a result, the use of these insecticides has been rapidly declining. However, the need for effective insect control has not changed. This has prompted researchers to develop novel methods of insect control.

The most widely used microbial pesticides are derived from the bacterium Bacillus thuringiensis (hereinafter B.t.). This bacterial agent is used to control a variety of leaf-eating caterpillars, Japanese beetles and mosquitos. U.S. Pat. No. 4,797,279 issued Jan. 10, 1989 to Karamata, et al., discloses hybrid bacterial cells comprising the gene coding for B.t. kurstaki delta-endotoxin and the gene coding for B.t. tenebrionis delta-endotoxin and their preparation. The B.t. hybrids are active against pests susceptible to B.t. kurstaki strains as well as against pests susceptible to B.t. tenebrionis strains. Generally, these hybrids have useful insecticidal properties which are superior to those observed by physical mixtures of the parent strains in terms of level of insecticidal activity, or in terms of spectrum of activity, or both. The insecticidal compositions comprising such microorganisms may be used to combat insects by applying the hybrids in an insecticidally effective amount to the insects or to their environment.

Another derivation from the bacterium B.t. was disclosed in European Patent Application, Publication No. 0 325 400 A1, issued to Gilroy and Wilcox. This invention relates to a hybrid toxin gene which is toxic to lepidopteran insects. Specifically, the invention comprises a hybrid delta-endotoxin gene comprising part of the B.t. var. kurstaki HD-73 toxin gene and part of the toxin gene from B.t. vat. kurstaki strain HD-1. The hybrid toxin gene (DNA) encoding a protein having activity against lepidopteran insects was disclosed.

The bacterium B.t. was also utilized for its insecticidal properties in European Patent Application, Publication No. 0 340 948, issued to Wilcox, et al. This invention concerns hybrid pesticidal toxins which are produced by the fusion of an insect gut epithelial cell recognition region of a B.t. gene to diphtheria toxin B chain to prepare a hybrid B.t. toxin which is active against lepidopteran insects. It was suggested that the hybrid B.t. gene may be inserted into a plant or cloned into a baculovirus to produce a toxin which can be recovered. Alternatively, the host containing the hybrid B.t. gene can be used as an insecticide by direct application to the environment of the targeted insect.

In the search for insecticidal compounds, scorpion venom was identified as a possible source of compounds providing insecticidal properties. Two insect selective toxins isolated from the venom of the scorpion Leiurus quinquestriatus quinquestriatus were revealed in Zlotkin, et al., "An Excitatory and a Depressant Insect Toxin from Scorpion Venom both Affect Sodium Conductance and Possess a Common Binding Site," Arch Biochem and Biophysics, 240:877–87 (1985). In a study related to their chemical and pharmacological properties, it was revealed that one toxin induced fast excitatory contractive paralysis of fly larvae and the other induced slow depressant flaccid paralysis. Both affected sodium conductance.

Canadian Patent 2,005,658 issued Jun. 19, 1990 to Zlotkin, et al., discloses an insecticidally effective protein derived from the scorpion Leiurus quinquestriatus hebraeus. In this invention, the venom is lyophilized and separated into fractions. The fraction with the highest toxicity to larvae and the lowest toxicity to mice was subjected to further purification and the final product is that referred to as "LqhP35".

Grishin, "Toxic components from Butbus eupeus and Lycosa singoriensis venoms," Shemyakin Institute of Bioorganic Chemistry, USSR Academy of Sciences, Moscow 117988, GSP-1, USSR, discloses four toxins isolated from the venom of the scorpion Buthus eupeus which are toxic to insects. Also disclosed was the isolation and characterization of the toxic component of the venom of the tarantula Lycosa singoriensis. The crude venom was nontoxic to insects.

Corresponding with the research and developments related to various compositions having insecticidal properties, researchers worked to develop methods for producing insecticidal genes and introducing these to a targeted pest. U.S. Pat. No. 4,879,236, issued Nov. 7, 1989 to Smith and Summers, relates to a method for incorporating a selected gene coupled with a baculovirus promoter into a baculovirus genome to produce a recombinant baculovirus expression vector capable of expression of the selected gene in an insect cell. The method involves cleaving baculovirus DNA to produce a DNA fragment comprising a polyhedrin gene or portion thereof, including a polyhedrin promoter. To prepare a recombinant transfer vector, the DNA fragment is inserted into a cloning vehicle and then a selected gene is inserted into this modified cloning vehicle such that it is under the control of the polyhedrin promoter. The recombinant transfer vector is then contacted with wild type baculovirus DNA so as to effect homologous recombination and incorporation of the selected gene into the baculovirus genome. The baculovirus Autographa californica (AcMNPV) and its associated polyhedrin promoter were found to be useful in producing a viral expression vector capable of extremely high levels of expression of a selected gene in a eukaryotic host cell.

The inventors suggest that the expression vector might be used in a system for controlling insects by selecting a gene which produces a protein which is toxic to a specific insect or to a spectrum of insects and cloning that gene into the AcMNPV expression vector. They suggest that the vector could be applied to the plant or animal to be protected. The recombinant virus could invade the cells of the intestinal wall following ingestion by the insect and begin replication. An alternative suggestion is to insert the gene into the baculovirus genome so that it would be fused to the polyhedrin structural sequence in such a way that the polyhedrin coating would be dissociated by the alkaline conditions of the insect gut and the toxic product would be released.

A further method for producing insecticidal genes and introducing them to the target to be protected was disclosed in Cutler, "Electropotation: Being Developed to Transform Crops: Success with Model Crop Confirmed," *AG Biotech. News* vol. 7(5):3 & 17 (1990). This article teaches that DNA may be electroporated directly into germinating pollen and that pollen may be put back on the flower to form seeds which then grow into transformed plants. This method has been employed successfully in tobacco plants and may be successful in corn and alfalfa as well. This method may be easier than the electropotation of protoplasts because the ultimate goal is to pollinate the flowers and "let the flowers do the work" rather than to regenerate the plant. The process consists of collecting pollen, germinating it in a germinating medium for 30–60 minutes after which the pollen tube will start to come out of the pollen grain, adding the desired DNA to the liquid suspension containing the pollen, administering an electric shock to open pores in the pollen tube, washing the excess DNA away, and putting the altered pollen on the stigma of a plant and waiting until seeds are formed. This may be an easy method to move any gene into crop plants.

Art additional delivery system was disclosed in U.S. Pat. No. 4,861,595 issued Aug. 29, 1989 to Barnes and Edwards. This invention concerns the use of treated, substantially intact, microbial cells as a delivery system of protein compounds to animals and humans. The microbial cells initially produce a protein intracellularly via a homologous gene. The protein-producing microbe is treated by chemical or physical means while the cell is substantially intact. Manipulation of the treatment process produces a nonproliferative treated microbial cell without significant loss of the activity of the intracellular compound. Since the cell will not replicate and will have a stable cell wall which may then be broken down in a desired area of the digestive system of the animal or human, it allows the timed or targeted release of the products encapsulated by the subject invention. After suitable treatment, the protein-producing microbial cell itself is used as the delivery system so no purification of the produced compound is necessary. Any protein, polypeptide, amino acid, or compound, including insecticides, that may be produced by microbial means may be the starting material of the invention.

The possibility of using DNA technology to incorporate a synthetic gene which encodes a neurotoxin found in scorpion venom was explored in Carbonell, et al., "Synthesis of a gene coding for an insect-specific scorpion neurotoxin and attempts to express it using baculovirus vectors," *Gene* 73:409–18 (1988). This article teaches the possibility of using DNA technology to incorporate a synthetic gene which encodes a neurotoxin found in the venom of the scorpion, *Buthus eupeus*, into the baculovirus genome to improve baculovirus pesticides. Three methods of expression using the polyhedrin promoter-based AcMNPV expression system to effect toxin production were studied. Expression of the 36 codon gene alone provided minuscule production of the toxin. Some success was found with the attachment of a signal peptide to the toxin. Significant levels of protein were produced when the toxin gene was fused to the N-terminus of polyhedrin gene. However, production was ten to twenty-fold less than that observed for polyhedrin itself. The limitation to expression was not believed to be at the level of transcription but at the post-transcriptional level including translation and protein stability. Paralytic activity of the toxin products was not detected.

European Patent Application, publication number 0 431 829, discloses transgenic plants which effectively express in their cells an insect-specific toxin of an insect predator in an amount sufficient so as to cause toxicity to selective insects ingesting the plant tissues. The particular toxin described was isolated from the venom of the scorpion *Androctonus australis*.

Researchers have also been able to isolate toxins extracted from the venom of spiders. Geren, "Neurotoxins and Necrotoxins of Spider Venoms," *J. Toxicol.-Toxin Reviews* 5(2):161–170 (1986), reviews work related to neurotoxins and necrotoxins and suggests that spider venom molecules may provide models for specific insecticides.

U.S. Pat. No. 4,925,664 issued to Jackson and Parks on May 15, 1990, discloses methods of treating heart and neurological diseases by applying toxins derived from the spiders *Agelenopsis aperta* and *Hololena curta*. The toxins are also effective as specific calcium channel or excitatory amino acid receptor blockers that may be used against insects and related pests.

European Patent Application, publication number 0 395 357, discloses polyamines and polypeptides isolated from the venom of the spider *Agelenopsis aperta*. The polyamines antagonize excitatory amino acid neurotransmitters. The polypeptides and one of the polyamines block calcium channels in living cells of various organisms. The use of said calcium channel blockers in the control of invertebrate pests is suggested.

European Patent Application, publication number 0 374 940, discloses toxins isolated from the venom of the spider *Hololena curta*. The polypeptides are useful as insecticides and in pharmaceuticals, for example, as calcium channel and glutamate antagonists.

Bowers, et al., "Identification and purification of an irreversible presynaptic neurotoxin from the venom of the spider *Hololena curta*," *Proc. Natl. Acad. Sci.* 84:3506–3510 (1987), discloses a proteinaceous neurotoxin isolated from the venom of the spider *Hololena curta* and its inhibition of neuromuscular transmission in Drosophila larvae. The authors suggest that the toxin blocks presynaptic calcium channels in Drosophila motor neurons.

Quistad, et al., "Paralytic and Insecticidal Toxins from the Funnel Web Spider, *Hololena Curta*," *Toxicon* 29(3):329–336 (1991), describes one peptide and ten curtatoxins purified from venom of *Hololena curta* and the effect when injected into lepidopteran larvae.

Stapleton, et al., "Curtatoxins: Neurotoxic insecticidal polypeptides isolated form the funnel-web spider *Hololena curta*," *J. Biol. Chem.* 265(4):2054–2059 (1990), discloses three polypeptide neurotoxins isolated from the venom of the spider *Hololena curta* and the effect on the cricket *Acheta domestica*.

Quicks and Usherwood, "Extended Summaries Pesticides Group and Physicochemical and Biophysical Panel Symposium Novel Approaches in Agrochemical Research," *Pestic. Sci.* 20:315–317 (1987), discloses that toxins present in the venoms of parasitic wasps and in the venoms of some orb-web spiders cause rapid paralysis when injected into insects. The authors suggest that spider toxins are blockers of glutamate receptor gated, cation-selective membrane channels. The publication refers to low molecular weight toxins in Argiope and Araneus spider venoms as well as a toxin isolated from venom glands of the Joro spider, *Nephila clavata*.

Another study related to the properties of isolated spider venom toxins revealed the ability of low molecular weight factors isolated from funnel-web spider venoms to bind reversibly to calcium channels. WO 89/07608 issued Aug. 24, 1989 to Cherksey, et al., discloses that these active low molecular weight factors reversibly bind to calcium channels with sufficient specificity and affinity to extinguish calcium conductance in neurons and to permit isolation and purification of calcium channel structures. These venoms were found to be toxic to mammals.

Other applications of spider toxins were discussed in Jackson and Parks, "Spider Toxins: Recent Applications in Neurobiology," *Ann Rev Neurosci* 12:405–14 (1989). This article teaches that there is great heterogeneity in the toxins of different taxa. It recognizes that experiments have suggested species-specific properties of calcium channels and the spider venoms might provide calcium channel antagonists. The spider venoms discussed are found to affect vertebrates. The article also identifies spider venoms as possible sources of insect-specific toxins for agricultural applications.

Adams, et al., "Isolation and Biological Activity of Synaptic Toxins from the Venom of the Funnel Web Spider, *Agelenopsis Aperta*," in Insect Neurochemistry and Neurophysiology 1986, Borkovec and Gelman eds., Humana Press, New Jersey, 1986, teaches that multiple peptide toxins which antagonize synaptic transmission in insects have been isolated from the spider *Agelenopsis aperta*.

U.S. Pat. No. 4,855,405 issued Aug. 8, 1989 to Yoshioka, et al., discloses a receptor inhibitor obtained from Joro spider venom glands, and its manufacturing method. The compound has an insecticidal effect when insects contact the compound carried in a liquid or solid.

U.S. Pat. No. 4,918,107 issued Apr. 17, 1990 to Nakajima et al., relates to a compound which has glutamate receptor inhibitor activity, a process for preparing the same, and an insecticidal composition containing the same. The compound is carried in a liquid or solid carrier with a dispersing agent added and applied directly to the plant or animal to be protected. A low dosage is effective as an insecticide and has very low mammalian and fish toxicity and small adverse influence to the environment.

The use of baculoviruses as bioinsecticides has also been explored. The major deficit of wild type baculoviruses as bioinsecticides is that they are slow-acting. Larvae that ingest wild type baculoviruses generally die within 5 to 7 days. The infected larvae continue to feed during a significant portion of this time and substantial crop damage can occur.

Due to a combination of problems associated with some synthetic insecticides, including toxicity, environmental hazards, and loss of efficacy due to resistance, there exists a continuing need for the development of novel means of invertebrate control, including the development of genetically engineered recombinant baculoviruses which express protein toxins capable of incapacitating the host more rapidly than the baculovirus infection per se.

SUMMARY OF THE INVENTION

There is provided by this invention a novel insecticidally effective peptide substantially purified and isolatable from Diguetia spider venom and agriculturally or horticulturally acceptable salts thereof.

The insecticidally effective peptides of this invention are believed to have a high degree of selectivity for invertebrates and, in particular, insects. Furthermore, the insecticidally effective peptides of this invention have been demonstrated to be highly effective insecticides against agriculturally important pests and thus are believed to represent an important contribution to the field of invertebrate pest control.

Further provided by this invention is a novel substantially isolated DNA sequence encoding an insecticidally effective peptide substantially isolatable from Diguetia spider venom.

Further provided by this invention is a novel recombinant expression vector comprising a DNA sequence encoding an insecticidally effective peptide substantially isolatable from Diguetia spider venom, wherein the vector is capable of effecting the expression of said coding sequence in transformed cells.

Further provided by this invention is a novel recombinant host cell transformed or transfected with a DNA sequence encoding an insecticidally effective peptide substantially isolatable from Diguetia spider venom in a manner allowing the host cell to express said peptide.

Further provided by this invention is a novel recombinant baculovirus expression vector, capable of expressing a DNA sequence encoding an insecticidally effective peptide substantially isolatable from Diguetia spider venom in a host or in a host insect cell.

Further provided by this invention is a novel method for producing an insecticidally effective peptide substantially isolatable from Diguetia spider venom, and the peptide produced thereby. The method comprises the steps of culturing recombinant host cells wherein a recombinant expression vector transformed or transfected in said host cells has a DNA sequence encoding an insecticidally effective peptide substantially isolatable from Diguetia spider venom, said vector being capable of effecting the expression of said coding sequence in transformed cells; and recovering said insecticidally effective peptide from the recombinant host cell culture.

Further provided by this invention is a novel transgenic plant comprising a DNA sequence encoding an insecticidally effective peptide substantially isolatable from Diguetia spider venom introduced into the germ line of said plant, or an ancestor of said plant, such that the trait of expression of said DNA sequence is inherited by subsequent generations of said plant through sexual propagation or asexual propagation.

Further provided by this invention is a novel method of controlling invertebrate pests comprising contacting said pests with an effective amount of an insecticidally effective peptide substantially isolatable from Diguetia spider venom and agriculturally or horticulturally acceptable salts thereof.

Further provided by this invention is a novel method of controlling invertebrate pests comprising contacting said pests with a recombinant baculovirus capable of expressing an effective amount of an insecticidally effective peptide substantially isolatable from Diguetia spider venom and agriculturally or horticulturally acceptable salts thereof.

Further provided by this invention is a novel insecticidal composition comprising an insecticidally effective amount of an insecticidally effective peptide substantially isolatable from Diguetia spider venom and agriculturally or horticulturally acceptable salts thereof in an agriculturally or horticulturally acceptable carrier therefor.

Further provided by this invention is a novel antibody substantially immunoreactive with an insecticidally effective peptide substantially isolatable from Diguetia spider venom and agriculturally or horticulturally acceptable salts thereof.

Further provided by this invention is a novel method of using the antibodies of this invention to detect the presence of an insecticidally effective peptide substantially isolatable from Diguetia spider venom comprising the steps of obtaining spider venom; contacting the spider venom with said antibodies coupled to a detectable label; and detecting the labeled antibody bound to said peptide.

Further provided by this invention is a novel method of using the antibodies of this invention to purify an insecticidally effective peptide substantially isolatable from Diguetia spider venom comprising the steps of conjugating the antibody to a solid support; contacting a solution containing said peptide with said antibody conjugated to said solid support whereby said peptide present in the solution attaches to said antibody; removing said peptide attached to said antibody conjugated to said solid support; and collecting said purified peptide.

Further provided by this invention is a novel DNA probe derived from a DNA sequence encoding an insecticidally effective peptide substantially isolatable from Diguetia spider venom.

Further provided by this invention is a novel method of detecting the presence of nucleic acid encoding an insecticidally effective peptide substantially isolatable from Diguetia spider venom comprising the steps of obtaining spider nucleic acids; contacting said nucleic acids with the DNA probe of this invention and detecting said probe bound to said nucleic acid.

DETAILED DESCRIPTION OF THE INVENTION

A. Definitions

Figure 1:
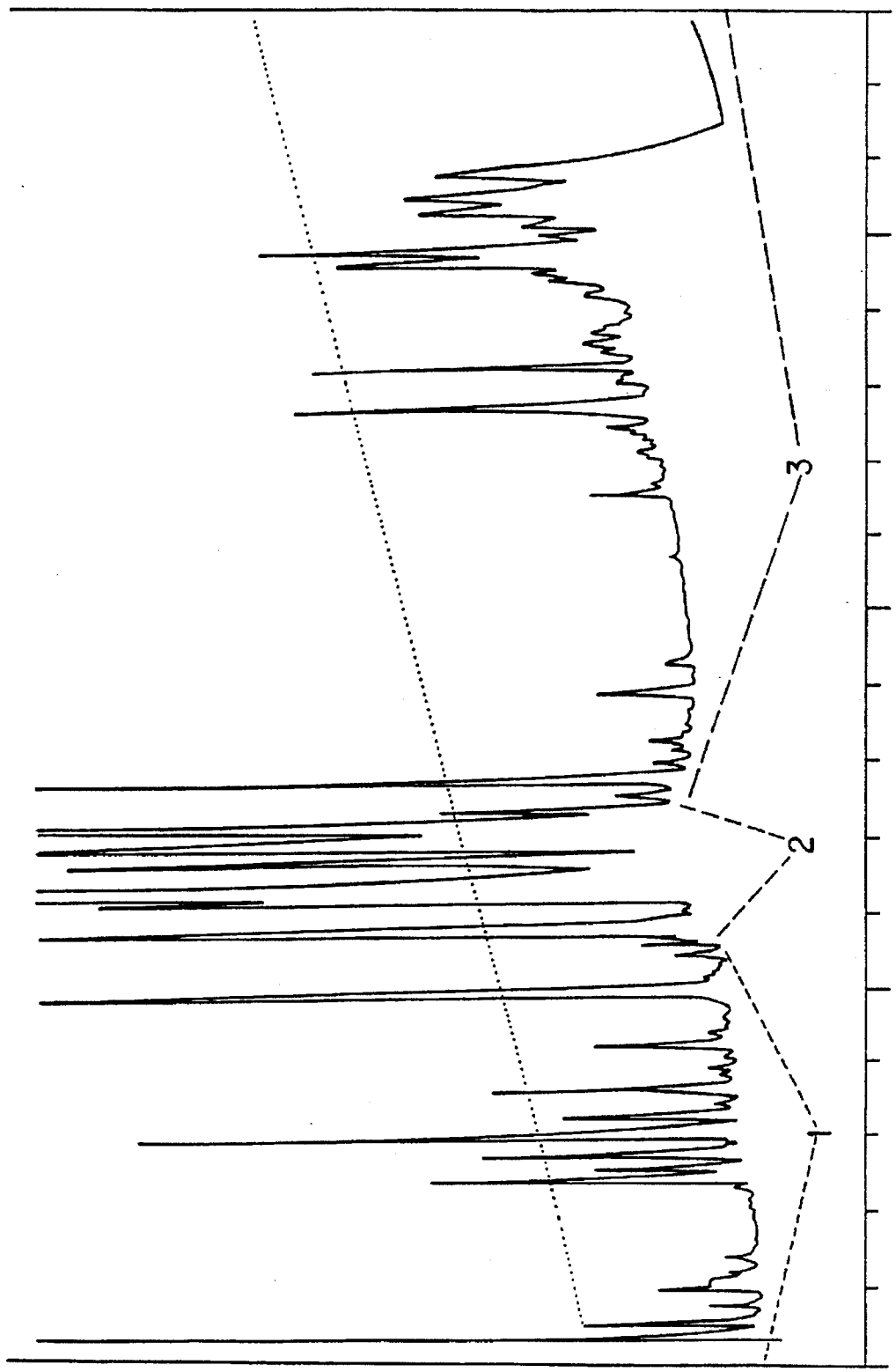
FIG. 1 depicts the RP HPLC of whole *Diguetia canities* venom using a gradient of 0.1% TFA to acetonitrile showing the three groups of components tested in mice. Fraction 2 represents the TBW active components.

As used herein, "an insecticidally effective peptide substantially isolatable from Diguetia spider venom" includes insecticidally effective peptides, as well as insecticidally effective fragments of said peptides, from any source so long as the peptide could have been substantially isolated from Diguetia by any of the techniques known to those in the art. Such sources include, for example, recombinantly produced insecticidally effective peptides.

As used herein, "expression vector" includes vectors which are capable of expressing DNA sequences contained therein, where such sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA which, in their vector form are not bound to the chromosome. "Plasmid" and "vector" are used interchangeably as the plasmid is the most commonly used form of vector. However, the invention is intended to include such other forms of expression vectors which serve equivalent functions and which become known in the art subsequently hereto.

"Recombinant host cells" refers to cells which have been transformed with vectors constructed using recombinant DNA techniques.

The spider family Diguetidae currently consists of a single genus, Diguetia. Diguetia species are generally found in the southwestern United States (including California) and Mexico. These small spiders spin expansive, irregular webs on many kinds of plants and shrubs, including cacti. The various species of Diguetia are, like most spiders, general predators, readily consuming most types of prey insects they encounter.

Although the invention is not meant to be limited to any theoretical reasoning, the unusual symptomatology seen upon injection of the insecticidally effective peptides of this invention into insects is very similar to the symptoms seen when veratridine, an alkaloid $Na^+$ channel activator, or scorpion toxins from the family Buthidae and genus Butbus, known presynaptic $Na^+$ channel activators, are injected into insects. It is believed that said insecticidally effective peptides may be causing a partial depolarization of muscle and/or nerve membranes, possibly affecting $Na^+$ or $K^+$ channels. More specifically, it is believed that said insecticidally effective peptides induce repetitive burst discharges in nerves that are sensitive to block by tetrodotoxin. Thus, it is probably the voltage-sensitive sodium channel of nerve membranes that is the site of action of these peptides.

B. The Isolation of peptides from Diguetia venom

Spider venom can be removed from Diguetia by any method known such as venom gland extraction from the cephalothorax. However, in order to avoid impurities within the spider venom and the isolated toxins, the spider venom preferably is obtained by electrical stimulation of the spiders to cause release of the venom and subsequent suction to collect the released venom and prevent contamination of the venom by regurgitate or hemolymph as described in U.S. Pat. No. 4,925,664.

Once the spider venom is obtained by electrical milking techniques, it can be fractionated into its peptide (toxin) components using high performance liquid chromatography ("HPLC") or gel filtration chromatography or any other useful fractionation technique. In addition, it is frequently desirable for final fractionation of the spider venom to be performed by HPLC.

Thus, using the technique of electrically milking the spider coupled with gel filtration chromatography and/or high performance liquid chromatography and other related techniques such as hydrophobic interaction chromatography, it is possible to obtain substantially purified spider toxins. It will be appreciated, however, that other equivalent techniques may also be employed within the scope of the present invention in order to isolate spider toxins. The toxins thus isolated can be evaluated for amino acid sequence and insecticidal activity by methods known to those in the art.

C. Insecticidally effective peptides

This invention, in one of its aspects, provides an insecticidally effective peptide, and insecticidally effective fragments thereof, substantially purified and isolatable from Diguetia spider venom and agriculturally or horticulturally acceptable salts thereof.

Once an insecticidally effective, peptide-containing fraction has been isolated and purified as described herein, amino acid sequence determination can be performed in any way known to those in the art such as N-terminal amino acid sequencing and use of an automated amino acid sequencer.

It will be understood from this disclosure that additional insecticidally effective proteins are expected to be within the scope of the invention. That is, it is believed other insecticidally effective peptides are isolatable from Diguetia in addition to the three detailed herein. The following relates to a family of insecticidally effective proteins isolatable from Diguetia. Members of this family of insecticidally effective peptides isolated from Diguetia appear to share the following characteristics:

1) size: all range between about 6200 to about 7200 daltons and range from about 55 to about 65 amino acids in length;

2) conserved amino terminus: SEQ ID NOS:1, 3 and 5 are identical for the first five amino acids;

3) SEQ ID NOS:1, 3 and 5 have greater than 40% sequence homology;

4) SEQ ID NOS:1, 3 and 5 have about 7 or 8 cysteine residues;

5) clustering of genes: the genes for more than one of these toxins appear to be co-localized sections of genomic DNA possibly indicating that these genes may all have descended from a single ancestral gene.

More specifically, three insecticidally effective peptides have been isolated and characterized. First, DK 9.2 has been isolated and its amino acid sequence, as translated from the isolated cDNA, appears as defined in SEQ ID NO:1. Mass spectroscopy data suggest two isozymes containing a conservative substitution at position 26. One isozyme contains a threonine at position 26 and the other contains a glutamine at position 26. The glutamine isozyme is about 27 atomic mass units greater than the threonine isozyme. Hereinafter any reference to DK 9.2 should be interpreted as a reference to either and/or both isozymes. DK 9.2 is characterized by a molecular weight of about 6371–6397 daltons as determined by mass spectrometry and movement as a single peak on reverse phase HPLC. Second, DK 11 has been isolated and is characterized by a molecular weight of about 6700 daltons or about 6740 daltons as determined by mass spectrometry and movement as a single peak on reverse phase HPLC. More particularly, this active HPLC fraction has been identified to have an amino acid sequence, as translated from the isolated cDNA, as shown in SEQ ID NO:3. Finally, to date, a third member of this insecticidally effective protein family, DK 12, has been characterized by a molecular weight of about 7100 daltons or about 7080 daltons as determined by mass spectrometry and moves as a single peak on reverse phase HPLC. More particularly this active fraction has been tentatively shown to have an amino acid sequence as shown in SEQ ID NO:5. The three peptides isolated, corresponding to SEQ ID NOS:1, 3 and 5, exhibit substantially the same insecticidal activity. It is expected that other peptides having about 55 to 65 amino acids, greater than 40% sequence homology with SEQ ID NOS:1, 3 or 5; and approximately 7 or 8 cysteine residues, will exhibit substantially the same insecticidal activity. Such peptides may exist in nature or may be produced by methods of recombinant DNA technology known to those of ordinary skill in the art. Such peptides, whether naturally occurring or recombinantly produced, are contemplated as within the scope of this invention.

D. Identification of the coding sequence of insecticidally effective peptides of this invention In another aspect of this invention, a substantially isolated DNA sequence encoding an insecticidally effective peptide substantially isolatable from Diguetia spider venom is provided.

Employing the partial amino acid sequence data obtained as described above, the genes responsible for the production of proteins isolatable from the spider can be isolated and identified. Numerous methods are available to obtain the gene responsible for the production of a peptide. Examples include Fuqua, S. et al., "A simple PCR method for detection and cloning low abundant transcript", *Biotechnique*, Vol. 9, No. 2 (Aug 1990); Frohman, M. A., "RACE: Rapid amplification of cDNA ends", *PCR protocols*, ed. Innis et al., Academic Press, San Diego, Calif., (1990) and U.S. Pat. No. 4,703,008 "DNA Sequences Encoding Erythropoietin" which patent is incorporated by reference.

Briefly, a DNA molecule is synthesized which encodes the determined amino acid sequence or which represents the complementary DNA strand to such a DNA molecule which encodes the determined amino acid sequence. This synthetic DNA molecule may then be used to probe for DNA sequence homology in cell clones containing recombinant DNA molecules comprising, in part, DNA sequences derived from the genomic DNA of an organism such as a spider or derived from cDNA copies of mRNA molecules isolated from cells or tissues of an organism such as a spider. Generally, DNA molecules of fifteen (15) nucleotides or more are required for unique identification of an homologous DNA, said number requiring unique determination of at least five (5) amino acids in sequence. It will be appreciated that the number of different DNA molecules which can encode the determined amino acid sequence may be very large since each amino acid may be encoded for by up to six (6) unique trinucleotide DNA sequences or codons. Therefore, it is impractical to test all possible synthetic DNA probes individually and pools of several such DNA molecules are used concomitantly as probes. The production of such pools which are referred to as "degenerate" probes is well known in the art. It will also be appreciated that while only one DNA molecule in the probe mixture will have an exact sequence homology to the gene of interest, several of the synthetic DNA molecules in the pool may be capable of uniquely identifying said gene since only a high degree of homology is required. Therefore, successful isolation of the gene of interest may be accomplished with synthetic DNA probe pools which do not contain all possible DNA probe sequences. In general, codons which are infrequently utilized by the organism need not be represented in the probe pool. In fact, a single sequence DNA probe may be produced by including only the DNA codons most frequently utilized by the organism for each amino acid, although, it will be appreciated that this approach is not always successful.

One technique to identify a gene sequence employs the Polymerase Chain Reaction (PCR). See e.g., U.S. Pat. Nos. 4,683,195 and 4,683,202 which patents are incorporated by reference as if fully set forth herein. Essentially PCR allows the production of a selected DNA sequence when the two terminal portions of the sequence are known. Primers, or oligonucleotide probes, are obtained which correspond to each end of the sequence of interest. Using PCR, the central portion of the DNA sequence is then synthetically produced.

In one such method of employing PCR to obtain the gene which encodes a unique spider venom gene, RNA is isolated from the spider and purified. A deoxythymidylate-tailed oligonucleotide is then used as a primer in order to reverse transcribe the spider RNA into cDNA. A synthetic DNA molecule or mixture of synthetic DNA molecules as in the degenerate probe described above is then prepared which can encode the amino-terminal amino acid sequence of the venom protein as previously determined. This DNA mixture is used together with the deoxythymidylate-tailed oligo-nucleotide to prime a PCR reaction. Because the synthetic DNA mixture used to prime the PCR reaction is specific to the desired mRNA sequence, only the desired cDNA will be effectively amplified. The resultant product represents an amplified cDNA which can be ligated to any of a number of known cloning vectors. Not withstanding this, it will be appreciated that "families" of peptides may exist in spider venoms which will have similar amino acid sequences and that in such cases, the use of mixed oligonucleotide primer sequences may result in the amplification of one or more of the related cDNAs encoding these related peptides. Genes encoding related peptides are also within the scope of the invention as the related peptides also have useful insecticidal activities.

Finally, the produced cDNA sequence can be cloned into an appropriate vector using conventional techniques, analyzed and the nucleotide base sequence determined. DNA sequences, encoding insecticidally effective proteins, are presented e.g. in SEQ ID NO:2 and 4. A direct amino acid translation of these PCR products will reveal that they corresponded to the complete coding sequence for the mature protein.

In addition to the cDNA encoding mature DK 9.2 the cDNA sequence upstream of the DK 9.2 encoding sequence was cloned and sequenced (SEQ ID NO:7). Translation of the complete mRNA revealed that DK 9.2 is synthesized as a precursor protein comprising a signal peptide, propeptide and the mature toxin. The function of the signal peptide is thought to be important for targeting the synthesized polypeptide for secretion. A signal sequence plays an important role in ensuring the proper localization of a newly synthesized protein. Generally they provide "topogenic signals" (Blobel, G. Proc.Nat.Acad.Sci., U.S.A. 77, 1496–1500 (1980), which target the attached protein sequence to various destinations within or external to the cell. This is particularly important for secreted proteins whose target sites are extracellular. It is also helpful for recombinant protein production as it can be easier to purify an expressed protein from the extracellular media rather than having to lyse the cells and purify from a whole cell extract. The signal peptide encoded by the cDNA coding for the precursor protein of DK 9.2 is believed to be comprised of 17 amino acids of the following sequence:

Met—Lys—Val—Phe—Val—Val—Leu—Leu—Cys—Leu—Ser—Leu—Ala—Ala—Val—Tyr—Ala

In addition to the signal peptide, translation of the mRNA located upstream of the DK 9.2 encoding sequence revealed a propeptide. The function of the propeptide sequence is unknown. The propeptide is a 21 amino acid peptide of the following sequence:

—Leu—Glu—Glu—Arg—Leu—Asp—Lys—Asp—Ala—Asp—Ile

—Met—Leu—Asp—Ser—Pro—Ala—Asp—Met—Glu—Arg—

These precursor peptides, or prepro sequence, may contribute greatly to the stability, expression and folding of DK 9.2 or other recombinant proteins when expressed in vivo and/or in vitro. That these sequences or portions thereof could prove useful in the expression of other molecules, for example in a gene construct, is also anticipated. As part of this invention we will also supply data to confirm that other signal and/or propeptide sequences could be used for the expression of recombinant DK 9.2.

E. Recombinant expression

Further provided by this invention is a recombinant expression vector comprising a DNA sequence which encodes an insecticidally effective peptide substantially isolatable from Diguetia spider venom. The vector is capable of effecting the expression of the coding sequence in transformed cells. Also provided by the invention are recombinant host cells transformed or transfected with a DNA sequence encoding an insecticidally effective peptide substantially isolatable from Diguetia spider venom in a manner allowing the host cell to express the peptide.

Provision of a suitable DNA sequence encoding the desired protein permits the production of the protein using recombinant techniques now known in the art. The coding sequence can be obtained by retrieving a cDNA or genomic sequence from a native source of the protein or can be prepared synthetically using the accurate amino acid sequence determined from the nucleotide sequence of the gene. When the coding DNA is prepared synthetically, advantage can be taken of known codon preferences of the intended host.

Expression systems containing the requisite control sequences, such as promoters, and preferably enhancers and termination controls, are readily available and known in the art for a variety of hosts. See e.g., Sambrook et al., *Molecular Cloning a Laboratory Manual*, Second Ed. Cold Spring Harbor Press (1989).

Thus, the desired proteins can be prepared in both procaryotic and eucaryotic systems, resulting, in the case of many proteins, in a spectrum of processed forms.

The most commonly used procaryotic system remains *E. coli*, although other systems such as *B. subtilis* and Pseudomonas are also expected to be useful. Suitable control sequences for procaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in procaryotic hosts in this matter, the signal sequence is removed upon secretion.

A wide variety of eucaryotic hosts are also now available for production of recombinant foreign proteins. As in bacteria, eucaryotic hosts may be transformed with expression systems which produce the desired protein directly, but more commonly signal sequences are provided to effect the secretion of the protein. Eucaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth.

Commonly used eucaryotic systems include yeast, insect cells, mammalian cells, arian cells, and cells of higher plants. The list is not exhaustive. Suitable promoters are available which are compatible and operable for use in each of these host types as well as are termination sequences and enhancers, as e.g. the baculovirus polyhedrin promoter. As above, promoters can be either constitutive or inducible. For example, in mammalian systems, the MTII promoter can be induced by the addition of heavy metal ions.

The particulars for the construction of expression systems suitable for desired hosts are known to those in the art. For recombinant production of the protein, the DNA encoding it is suitably ligated into the expression system of choice, and the system is then transformed into the compatible host which is then cultured and maintained under conditions wherein expression of the foreign gene takes place. The insecticidally effective protein of this invention thus produced is recovered from the culture, either by lysing the cells or from the culture medium as appropriate and known to those in the art.

It is understood that minor modifications of primary amino acid sequence may result in proteins which have substantially equivalent or enhanced activity as compared to the peptides exemplified herein. These modifications may be deliberate, as through site directed mutagenesis, or may be accidental such as through mutations in hosts which produce the peptide of the invention; all these modifications are included so long as insecticidal activity is retained. A "mutation" in a protein alters its primary structure (relative to the commonly occurring or specifically described protein) due to changes in the nucleotide sequence of the DNA which encodes it. These mutations specifically include allelic variants. Mutational changes in the primary structure of a protein result from deletions, additions, or substitutions. A "deletion" is defined as a polypeptide in which one or more internal amino acid residues are absent as compared to the native sequence. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar and/or aromatic. It is generally preferred that encoded peptides differing from the native form contain substituted codons for amino acids which are from the same group as that of the amino acid replaced.

Thus, in general, the basic amino acids Lys, Arg, and His are interchangeable; the acidic amino acids Asp and Glu are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable.

While Pro is a nonpolar neutral amino acid, it represents difficulties because of its effects on conformation, and substitutions by or for Pro are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by codons for amino acids from different classes may also be useful.

Because recombinant materials for the proteins of the invention are provided, these proteins can be made by recombinant techniques as well as by automated amino acid synthesizers. Because of the variety of post-translational characteristics conferred by various host cells, various modifications for the naturally-occurring proteins will also be obtained. A "modified" protein differs from the unmodified protein as a result of post-translational events which change the glycosylation, amidation or lipidation pattern, or the primary, secondary, or tertiary structure of the protein and are of course included within the scope of the invention as claimed.

It should be further noted that if the proteins herein, such as SEQ ID NO:1 are made synthetically, substitution by amino acids which are not encoded by the gene may also be made. Alternative residues include, for example, the ω amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

F. Transgenic plants

Further provided by this invention are transgenic plants comprising a DNA sequence encoding an insecticidally effective peptide substantially isolatable from Diguetia spider venom introduced into the germ line of the plant, such that the trait of expression of the DNA sequence is inherited by subsequent generations of the plant through sexual propagation or asexual propagation.

Genes encoding the insecticidally effective peptides according to the present invention can be introduced into a plant by genetic engineering techniques, which upon production of the peptide in the plant cell is expected to be useful as a means for controlling insect pests. Therefore, it is possible to produce a plant that is more insect-tolerant than the naturally occurring variety.

The coding region for an insecticidally effective peptide gene that may be used to transform a plant may be the full-length or partial active length of the gene. It is necessary, however, that the genetic sequence coding for the peptide be expressed, and produced, as a functional peptide in the resulting plant cell. It is believed that DNA from both genomic DNA and cDNA and synthetic DNA encoding an insecticidally effective peptide may be used to transform. Further, a gene may be constructed partially of a cDNA clone, partially of a genomic clone, and partially of a synthetic gene and various combinations thereof. In addition, the DNA coding for a peptide gene may comprise portions from various species other than from the source of the isolated peptide.

Furthermore, it is believed the insecticidally effective peptide may be combined with another compound or compounds to produce unexpected insecticidal properties in the transformed plant, containing chimeric genes, expressing the compounds. These other compounds can include protease inhibitors, for example, which have oral toxicity to insects or polypeptides from *Bacillus thuringiensis*. The *B. thuringiensis* protein causes changes in potassium permeability of the insect gut cell membrane and is postulated to generate small pores in the membrane. Other pore-forming proteins could also be used in combination with the insecticidally effective peptides. Examples of such pore-forming proteins are the magainins, the cecropins, the attacins, melittin, gramicidin S, sodium channel proteins and synthetic fragments, the α-toxin of *Staphylococcus aureus*, apolipoproteins and their fragments, alamethicin and a variety of synthetic amphipathic peptides. Lectins which bind to cell membranes and enhance endocytosis are another class of proteins which could be used in combination with the insecticidally effective peptides of this invention to genetically modify plants for insect resistance.

The promoter of the peptide gene is expected to be useful in expressing the chimeric genetic sequence, however, other promoters are also expected to be useful. An efficient plant promoter that may be useful is an overproducing promoter. This promoter in operable linkage with the genetic sequence for the peptide should be capable of promoting expression of the peptide such that the transformed plant has increased tolerance to insect pests. Overproducing plant promoters that are expected to be useful in this invention are known.

The chimeric genetic sequence comprising an insecticidally effective peptide gene operably linked to a promoter can be ligated into a suitable cloning vector to transform the desired plant. In general, plasmid or viral (bacteriophage) vectors containing replication and control sequences derived from species compatible with the host cell are used. The cloning vector will typically carry a replication origin, as well as specific genes that are capable Of providing phenotypic selection markers in transformed host cells, typically resistance to antibiotics. The transforming vectors can be selected by these phenotypic markers after transformation in a host cell.

Most cells that are expected to be useful include procaryotes, including bacterial hosts such as *E. coli, Salmonella ryphimurium*, and *Serratia marcescens;* and eucaryotic hosts such as yeast or filamentous fungi.

The cloning vector and host cell transformed with the vector are generally used to increase the copy number of the vector. With an increased copy number, the vectors containing the peptide gene can be isolated and, for example, used to introduce the genetic sequences described herein into the plant or other host cells.

Methods to produce plants expressing foreign genes are known. For example, plant tissue can be transformed by direct infection of or co-cultivation of plants, plant tissue or cells with *A. tumefaciens;* direct gene transfer of exogenous DNA to protoplasts; incubation with PEG; microinjection and microprojectile bombardment.

Transformation in tobacco by electropotation a technique described in *Ag Biotechnology News*, Vol. 7 p. 3 and 17 (Sept/Oct 1990) has been confirmed. In this technique, plant protoplasts are electroporated in the presence of plasmids containing the insecticidally effective peptide genetic construct. Electrical impulses of high field strength reversibly permeabilize biomembranes allowing the introduction of the plasmids. Electroporated plant protoplasts reform the cell wall, divide, and form plant callus. Selection of the transformed plant cells with the expressed insecticidally effective peptide can be accomplished using the phenotypic markers as described above. The exogenous DNA may be added to the protoplasts in any form such as, for example, naked linear, circular or supercoiled DNA, DNA encapsulated in liposomes, DNA in spheroplasts, DNA in other plant protoplasts, DNA complexed with salts, and the like.

All plant cells which can be transformed by Agrobacterium and whole plants regenerated from the transformed cells can also be transformed according to the invention so to produce transformed whole plants which contain the transferred insecticidally effective peptide gene. Transformation in rice has been confirmed by D. M. Raineri et al., "Agrobacterium-mediated transformation of rice (*Oryza sativa* 1.)", *Biotechnology*, Vol. 8, pp 33–38 (January 1990).

Another method of introducing the insecticidally effective peptide gene into plant cells is to infect a plant cell with *A. tumefaciens* transformed with the insecticidally effective peptide gene. Under appropriate conditions known in the art, the transformed plant cells are grown to form shoots, roots, and develop further into transformed plants. The insecticidally effective peptide genetic sequences can be introduced into appropriate plant cells, for example, by means of the Ti plasmid of *A. tumefaciens*. The Ti plasmid is transmitted to plant cells on infection by *A. tumefaciens* and is stably integrated into the plant genome.

Ti plasmids contain two regions believed essential for the production of transformed cells. One of these, named transfer DNA (T DNA), induces tumor formation. The other, termed virulent region, is essential for the formation but not maintenance of tumors. The T DNA region, which transfers to the plant genome, can be increased in size by the insertion of an enzyme's genetic sequence without its transferring ability being affected. By removing the tumor-causing genes so that they no longer interfere, the modified Ti plasmid can then be used as a vector for the transfer of the gene constructs of the invention into an appropriate plant cell.

The genetic material may also be transferred into the plant cell by using polyethylene glycol (PEG) which forms a precipitation complex with the genetic material that is taken up by the cell.

Transfer of DNA into plant cells can also be achieved by injection into isolated protoplasts, cultured cells and tissues and injection into meristematic tissues of seedlings and plants. Transgenic plants and progeny therefrom are obtained by conventional methods known in the art.

Another method to introduce foreign DNA sequences into plant cells comprises the attachment of the DNA to particles which are then forced into plant cells by means of a shooting device, "gene guns". Any plant tissue or plant organ may be used as the target for this procedure, including but not limited to embryos, apical and other meristems, buds, somatic and sexual tissues in vivo and in vitro. Transgenic cells and callus are selected following established procedures. Targeted tissues are induced to form somatic embryos or regenerate shoots to give transgenic plants according to established procedures known in the art. The appropriate procedure may be chosen in accordance with the plant species used. Transgenic maize plants have been prepared by using high-velocity microprojectiles to transfer genes into embryogenic cells. "Inheritance and expression of chimeric genes in the progeny of transgenic maize plants", *Biotechnology*, Vol. 8, pp 833–838 (September 1990).

The regenerated plant may be chimeric with respect to the incorporated foreign DNA. If the cells containing the foreign DNA develop into either micro- or macrospores, the integrated foreign DNA will be transmitted to sexual progeny. If the cells containing the foreign DNA are somatic cells of the plant, non-chimeric transgenic plants are produced by conventional methods of vegetative (asexual) propagation either in vivo, from buds or stem cuttings, or in vitro following established procedures known in the art. Such procedures may be chosen in accordance with the plant species used.

After transformation of the plant cell or plant, those plant cells or plants transformed so that the peptide is expressed, can be selected by an appropriate phenotypic marker. These phenotypic markers include, but are not limited to, antibiotic resistance. Other phenotypic markers are known in the art and may be used in this invention.

Due to the variety of different transformation systems, all plant types can in principle be transformed so that they express an insecticidally effective peptide of the present invention.

There is an increasing body of evidence that practically all plants can be regenerated from cultured cells or tissues, including but not limited to all major cereal crop species, sugar cane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. There is growing evidence now that certain monocots can be transformed by Agrobacterium. Using novel experimental approaches that have now become available, cereal and grass species may also be transformable.

Additional plant genera that may be transformed by Agrobacterium include Ipomoea, Passiflora, Cyclamen, Malus, Prunus, Rosa, Rubus, Populus, Santalion, Allium, Lilium, Nacissus, Ananas, Arachis, Phaseolus, and Pisum.

Regeneration varies from species to species of plants, but generally a suspension of transformed protoplasts containing multiple copies of the insecticidally effective peptide gene is first provided. Embryo formation can then be induced from the protoplast suspensions, to the stage of ripening and germination as natural embryos. The culture media will generally contain various amino acids and hormones. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, can be selfed to produce an inbred plant. The inbred plant produces seed containing the gene for the insecticidally effective peptide. These seeds can be grown to produce plants that express the insecticidally effective peptide. The inbreds can, e.g., be used to develop insect tolerant hybrids. In this method, an insect tolerant inbred line is crossed with another inbred line to produce the hybrid.

In diploid plants, typically one parent may be transformed by the insecticidally effective peptide (toxin) genetic sequence and the other parent is the wild type. After crossing the parents, the first generation hybrids ($F_1$) will show a distribution of ½ toxin/wild type: ½ toxin/wild type. These first generation hybrids ($F_1$) are selfed to produce second generation hybrids ($F_2$). The genetic distribution of the $F_2$ hybrids is ¼ toxin/toxin: ½ toxin/wild type: ¼ wild type/wild type. The $F_2$ hybrids with the genetic makeup of toxin/toxin are chosen as the insect tolerant plants.

As used herein, variant describes phenotypic changes that are stable and heritable, including heritable variation that is sexually transmitted to progeny of plants, provided that the variant still expresses an insecticidally effective peptide of the invention. Also, as used herein, mutant describes variation as a result of environmental conditions, such as radiation, or as a result of genetic variation in which a trait is transmitted meiotically according to well-established laws of inheritance. The mutant plant, however, must still express the peptide of the invention.

In general, the ideal insecticidally effective protein chosen to be expressed in a transgenic plant, will be one that is characterized by its safety to non-target insects and vertebrates. Expression systems will be chosen such that the level of expression affords insecticidal efficacy. Thus, this technical feasibility of obtaining such transgenic agriculturally important plants is expected to offer farmers an additional weapon to use in an integrated pest management system to reduce insect damage to crops in an environmentally responsible manner.

G. Application of the peptides as insecticides

The insecticidally effective peptides of this invention are believed to be useful in controlling invertebrate pests such as the order of Lepidoptera, by contacting the pests with an effective amount of a peptide of this invention. Conveniently, insects are the preferred pest.

Methods of contacting an invertebrate pest with a peptide to control said pests are known. Examples include synthetically encapsulating the protein for oral ingestion by the pest. Recombinant hosts expressing the proteins of this invention, such as *Pseudomonas fluorescens*, can be heat killed and applied to pests for subsequent oral ingestion and control.

Of course, methods of controlling invertebrate pests using the proteins of this invention can be used in combination with other methods of controlling pests. For example, the transgenic plants and *E. coli* mentioned above can be engineered to express other invertebrate toxins depending on the type of pests to be controlled and other important variables present.

An insecticidal composition comprising an insecticidally effective amount of a peptide according to this invention and agriculturally or horticulturally acceptable salts thereof in an agriculturally or horticulturally acceptable carrier therefor is also provided.

H. Antibodies to insecticidally effective peptides

Another aspect of this invention are antibodies to the insecticidally effective peptides of this invention. In the following description, reference will be made to various methodologies known to those skilled in the art of immunology for detecting and purifying peptides reactive with the antibodies described herein.

An antibody is said to be "capable of binding" a molecule if it is capable of specifically reacting with the molecule to thereby bind the molecule to the antibody. The term "epitope" is meant to refer to that portion of a peptide antigen which can be recognized and bound by an antibody. An antigen may have one or more than one epitope. An "antigen" is capable of inducing an animal to produce antibody capable of binding to an epitope of that antigen. The specific reaction referred to above is meant to indicate that the antigen will immunoreact, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an insect antibody.

The antibodies of the present invention may be prepared by any of a variety of methods. Methods for the production of such antibodies are well known and described fully in the literature. See e.g., Sambrook et al., "Molecular Cloning a laboratory manual", second ed. Cold Spring Harbor Press, Vol. 3, Ch. 18 (1989). For example, cells expressing the insecticidally effective peptide or a fragment thereof, can be administered to an animal in order to induce the production of sera containing polyclonal antibodies that are capable of binding the insecticidally effective peptide. Generally, an insecticidally effective peptide fragment is prepared and purified to render it substantially free of natural contaminants or an insecticidally effective peptide fragment is synthesized, according to means known in the art. Either the purified fragment or the synthesized fragment or a combination of purified natural fragments and/or synthesized fragment may be introduced into an animal in order to produce polyclonal antisera of greater specific activity.

Monoclonal antibodies can be prepared using known hybridoma technology. In general, such procedures involve immunizing an animal with an insecticidally effective peptide antigen. The splenocytes of such animals are extracted and fused with a suitable myeloma cell line. Any suitable myeloma cell line may be employed in accordance with the present invention. After fusion, the resulting hybridoma cells are selectively maintained in a suitable medium and then cloned by limiting dilution. The hybridoma cells obtained through such a selection are then assayed to identify clones which secrete antibodies capable of binding the insecticidally effective peptide antigen.

If the peptide source is impure, only some of the hybridoma cells will produce antibodies capable of binding to the peptide (other hybridoma cells will produce antibody capable of binding to the peptide contaminants). Thus, it may be necessary to screen among the hybridoma cells for those which are capable of secreting an antibody which is capable of binding to the peptide. Such screening is preferably accomplished by incubating a sample of the peptide (or venom) in the presence of monoclonal antibody secreted from each of a group of particular hybridoma cells and identifying any hybridoma cell capable of secreting an antibody which is able to neutralize or attenuate the ability of the venom to paralyze an insect. Once such a hybridoma cell has been identified, it may be clonally propagated by means known in the art in order to produce the peptide-specific monoclonal antibody.

To purify an insect selective toxin, native or recombinant, using antibody affinity chromatography, it is necessary to employ an antibody capable of binding to the insecticidally effective peptide. Generally, such an antibody will be a monoclonal antibody. Once a peptide-specific monoclonal antibody has been obtained, it may be immobilized by binding to a solid support and used to purify the peptide from natural venom or other sources using immunoaffinity chromatography in accordance to methods which are well known in the art. Such methods are capable of mediating a high degree of purification and of thereby producing a peptide which is substantially free of natural contaminants. As used herein, a peptide is said to be "substantially free of natural contaminants" if it is present in a form which lacks compounds with which it is naturally and normally associated (i.e. other proteins, lipids, carbohydrates, etc.).

Once the peptide has been purified, it can be used to immunize an animal (such as a mouse or rabbit) in order to elicit the production of peptide-specific polyclonal antibody.

DNA probes of suitable size, generally from 10 to 50 nucleotides, can be derived from a DNA sequence encoding an insecticidally effective peptide substantially isolatable from Diguetia spider venom. Such probes can be used to detect the presence of DNA encoding an insecticidally effective peptide substantially isolatable from Diguetia spider venom by contacting a venom with the DNA probe and detecting the probe conjugated to said DNA by ways known to those in the art.

I. Genetically engineered insecticidal microbes

The insecticidally effective peptide alone or in combination with another insect toxin is expected to be useful in potentiating or enhancing the toxicity of microbes such as baculoviruses and hybrid bacteria.

Several baculoviruses including those that infect *Heliothis virescens* (cotton bollworm), *Orgyia pseudotsugata* (Douglas fir tussock moth), *Lymantria dispar* (gypsy moth), *Autographa californica* (alfalfa looper), *Neodiprion sertifer* (European pine fly), and *Laspeyresia pomonella* (codling moth) have been registered in some countries and used as pesticides. Introduction of at least one insect-selective toxin into the genome is expected to significantly enhance the potency of such pesticides.

A recombinant expression vector expected to be particularly suitable for use in this invention is a baculovirus expression vector such as the type disclosed in U.S. Pat. No. 4,879,236, which patent is incorporated by reference as if fully set forth herein. See also Carbonell et al. "Synthesis of a gene coding for an insect-specific scorpion neurotoxin and attempts to express it using baculovirus vectors," *Gene*, 73:409–418 (1988). The vector is expected to be useful in a system where a DNA sequence encoding an insecticidally effective peptide substantially isolatable from Diguetia spider venom can be cloned into baculovirus such as *Autographa californica* (AcMNPV) expression vector as described in U.S. Pat. No. 4,879,236 and Miller et al., *Science*, 219, 715–721 (1983). The recombinant expression vector virus could then be applied to the plant or animal upon which the insect is a pest, and when the virus is ingested by the pest insect, the recombinant virus will invade the cells of the intestinal wall and begin replication. During replication, the gene for the insecticidally effective protein will be expressed, resulting in the disablement or death of the insect in a shorter period than if the insect had ingested the wild type AcMNPV virus.

A hybrid virus also expected to be useful is taught in European Patent Application 0 340 948. The hybrid virus expressing the DNA of this invention is expected to yield a virus having an altered insect host range. For example, fusion proteins could be expressed as a single polypeptide product of a hybrid gene consisting of DNA of this invention and a specific insect gut cell recognition protein to direct the expressed insecticidally effective peptide to the host insect target.

Various prokaryotic and eukaryotic microbes can be transformed to express a hybrid toxin gene encoding an insecticidally effective protein by the method taught in European Patent Application 0 325 400.

Hybrid bacterial cells, comprising a plasmid with the gene coding for the protein of this invention are expected to be useful in the method of this invention. Insects would be controlled by applying the hybrids to insects. See e.g., U.S. Pat. No. 4,797,279 which patent is incorporated by reference as if fully set forth herein.

Other examples of employing baculovirus that would be suitable for use in this invention are described in Tomalski et al., "Insect paralysis by baculovirus-mediated expression of a mite neurotoxin gene", *Nature*, 352: 82–85 (1991) and Stewart et al., "Construction of an improved baculovirus insecticide containing an insect-specific toxin gene", *Nature,* 352:85–88 (1991); McCutchen, et al., "Development of a recombinant Baculovirus expressing an insect seective Neurotoxin: Potential for Pest Control," *Biotechnology,* 9:848–851 (1991).

J. Cross-hybridization: DNA sequences as probes for related compounds.

DNA probes of suitable size, can be derived from a DNA sequence of this invention. Such probes can be used to detect the presence of nucleic acid encoding an insecticidally effective peptide of this invention by hybridization with nucleic acids from other sources. Screening with oligonucleotide probes encoding the signal sequence, fragments of the cDNA, or even the entire cDNA under conditions of reduced stringency will allow access to other active peptides with functional homology to the family of toxin molecules described herein. Sources of nucleic acids which would be good candidates for cross-hybridization with nucleotide probes generated from DNA sequences of this invention would include, but are not limited to spiders of the same genera but of different species, spiders of related genera, and spiders of the same genera but different locations.

K. Identification of A Promoter Sequence

Another aspect of this invention provides for the promoter sequence which controls the synthesis of DK 9.2 in the spider. The organization of the gene for DK 9.2 was examined by screening a genomic library with the mature toxin cDNA as probe. Analysis of the genomic DNA upstream of the transcriptional start (assumed to be the 5' end of the cDNA), does indicate the presence of a putative promoter. A DNA sequence for 421 base pairs of the promoter region is presented in SEQ ID NO:8. This putative promoter contains many of the essential control signals that are generally present in the region directly upstream of the translational start site. (For review of promoter control signals see McKnight et al., 1982. Transcriptional Control Signals of an Eucaryotic Protein-Coding Gene. *Science* 217:316.) A canonical TATA box appears at position -30 from the proposed transcriptional start site and is suggested to be important in controlling the start point for RNA synthesis. Further upstream there are two distal palindromic sequences, one of which contains the consensus CAAT box thought to be important for binding of the RNA polymerase II enzyme. It is anticipated that this promoter, or regions of this promoter will have utility in the transcription and expression of a variety of genes in plant, animal or bacterial cells, for example, in a recombinant construct.

EXAMPLES

The following examples are given to illustrate particular compositions and methods within the scope of the present invention but they are not intended to limit the scope of the present invention.

Materials and Methods

Spiders were collected from a known wild population and were identified at NPS Pharmaceuticals (Salt Lake City, Utah) as *Diguetia canities. Diguetia canities* spiders were electrically milked for venom using a method that employs safeguards to prevent contamination of venom by regurgitate or hemolymph.

Toxin Purification—Crude venom (stored at −80° C.) was thawed, mixed thoroughly and dissolved in 0.1% trifluoroacetic acid (TFA) prior to chromatography. Crude venom was fractionated by reverse phase liquid chromatography (RPLC) incorporating Beckman System Gold 126 solvent and 168 photodiode-array detector modules. Acetonitrile or isopropanol was used in combinations with TFA as an ion pairing reagent. The following columns, with guard columns of the same matrix, were used in the purifications: Dynamax 300 A RP $C_{18}$ column (25 cm ×4.6 mm i.d., 12 µm particle size), Vydac 300 A $C_{18}$ analytical column (25 cm ×4.6 mm i.d., 5 µm particle), and Vydac 300 A $C_{18}$ semi-preparative column (25 cm ×10 mm i.d. 5 µm particle size). Peak detection was accomplished by monitoring at 220 nm and collecting fractions with a GILSON 208 microfraction collector. All fractions were lyophilized to dryness following fractionation and stored at −80° C.

Fast Atom Bombardment Mass Spectrometry (FAB-MS)—Mass spectra were recorded at the University of Illinois on VG instruments ZAB-SE mass spectrometer under standard FAB conditions (xenon gas, resolution 1000, accelerating voltage 8 kV, source temperature 40° C.). Samples (about 1 µg) were analyzed in 4 µl thioglycerol containing 25% aqueous TFA (1.0%).

Example 1

Initial Fractionation and Identification of Insecticidal Peptide-Containing Fractions from *Diguetia canities* Whole Venom Lyophilized whole venom, 25 µl, obtained from *Diguetia canities* as described previously, was dissolved in 0.1% trifluoroacetic acid (TFA) and was subjected to fractionation by reverse phase liquid chromatography on a semi-preparative Vydac RP $C_{18}$ column, eluting at a flow rate of 3.5 ml per minute. A linear gradient of eluant was used beginning with an 85:15 mixture of aqueous 0.1% TFA: 50% acetonitrile, 0.1% TFA and ending with a 50:50 mixture after 180 minutes.

| Fraction | Retention Time (approx. minutes) |
|---|---|
| 1 | 3.2 |
| 4 | 29.6 |
| 6 | 48.2 |
| 8 | 57.1 |
| 9 | 62.8 |
| 10 | 66.4 |
| 11 | 68.7 |
| 12 | 71.4 |
| 13 | 77.1 |
| 16 | 126.1 |
| 17 | 131.4 |

Each fraction was concentrated by lyophilization from the eluant followed by lyophilization from water. The residues were stored at −80° C. Each fraction was dissolved in 25 µl of a buffered physiological saline solution for insecticidal evaluation. The insecticidal activity of some fractions was confirmed by testing against the tobacco budworm (*Heliothis virescens*) "TBW" (Table I).

TBW larvae, five individuals for each fraction, were injected with 3 µl of the test solution using a 50 µl Hamilton syringe fitted with a 33 gauge needle and a PB 600 repeating microdispenser. The injections were made by insertion of the needle into the lateral midline of the abdomen (near one of the prolegs) at a shallow angle in order to avoid damaging internal organs. Following the injection each insect was placed into a separate container containing artificial diet. Observations were made periodically; paralysis was measured at 24 hours following injection. Mean body mass of 0.3 gm for tobacco budworms was used in calculating doses. A set of control insects was injected with the buffered saline solution only.

Paralysis developed gradually and was preceded by a period of pronounced muscle spasms. In severe cases these spasms began within 15–30 minutes of injection and gradually increased in intensity until the larvae were completely incapacitated. Tremoring sometimes persisted for more than 48 hours after injection. This occasionally occurred even when a sublethal dose was administered and the larvae eventually recovered. The severity of tremoring was the most reliable indicator of toxicity; larvae affected to the point of total paralysis and/or body contraction did not recover.

TABLE I

Toxicity of *Diguetia canities* Whole Venom
RPLC Fractions on TBW (7.5 WVE/gm of insect)**

| Fraction | % paralysis* initial | % paralysis 24 hr |
| --- | --- | --- |
| 1 | 0 | 0 |
| 4 | 0 | 0 |
| 6 | 0 | 0 |
| 8 | 100 | 100 |
| 9 | 100 | 100 |
| 10 | 100 | 100 |
| 11 | 100 | 100 |
| 12 | 100 | 100 |
| 13 | 0 | 0 |
| 16 | 0 | 0 |
| 17 | 0 | 0 |
| control | 0 | 0 |

*Paralysis is defined as the inability of the insect to right itself when turned on its side or back.
**WVE, whole venom equivalent is the amount of any toxin that is normally present in one microliter of whole, milked venom; 5 WVE from a 25 microliter separation is 20% of the recovered residue.

Fractions from preliminary separations of *D. canities* venom were also tested in the house fly (*Musca domestica*) and the house cricket (*Acheta domestica*). These insects were injected (using the same general protocol used for TBW injections) with reversed-phase HPLC fractions from *D. canities* venom at doses of 0.5 WVE per fly (n=5) and 0.5 WVE per cricket (n=4). In crickets, the fractions corresponding to the venom components with TBW activity caused either 75% or 100% paralysis within 24 hours; only one other fraction was active (control insects were unaffected). In house flies, the same fractions caused either 80% or 100% paralysis within 24 hours; controls were unaffected. Paralysis in both crickets and house flies was of the same excitatory type noted in TBW.

Example 2

Purification of *Diguetia canities* Fraction 9

The major components of the TBW active Fraction 9 were purified to homogeneity (one visual band each by SDS-PAGE electrophoresis, approximately in the molecular weight range of 6,500 daltons) by one additional chromatography through Vydac RP $C_{18}$ (25 cm×10 mm i.d.) using a linear (1.0%/min) solvent gradient of iso-propanol/0.1% TFA at 3.5 ml/min, monitoring at 220 nm.

Peak detection and fraction collection were accomplished as described in Example 1. Two fractions were collected: the first eluting at 21.81 minutes (Fraction 9.1) and the second eluting at 22.39 minutes (Fraction 9.2).

Fractions 9.1 and 9.2 were concentrated by lyophilization from the eluant followed by lyophilization from water, leaving residues 9.1 and 9.2, respectively. Purity of the lyophilized fractions was estimated to be at least 99%. Residue 9.2 obtained from 25 µl of whole venom was estimated to contain approximately 6 µg of pure protein.

Residue 9.2 was tested for insecticidal activity against tobacco budworm as described in Example 1 by injecting each of five insects with 6.3 µg of residue in a buffered saline solution and five insects as controls with the buffered saline solution only. After 24 hours and 48 hours the insects were examined. At the 24 hr reading all those insects treated with the residue 9.2 solution were paralyzed and subsequently died while the control insects appeared normal. No changes were noticed at 48 hr.

Analysis of this polypeptide by fast atom bombardment mass spectrometry indicated a molecular weight of 6371±2. N-terminal amino acid sequence analysis resulted in a partial amino acid sequence for residue 9.2 substantially as shown in SEQ ID NO:1, amino acids 1–33.

As shown in Table II, the $PD_{50}$ doses of the Diguetia toxins in TBW larvae range from 0.38 nmol/gm (DK9.2) to 0.71 nmol/gm (DK11) to 3.18 nmol/gm (DK12). $PD_{50}$ values were calculated by probit analysis, using the method of Raymond

TABLE II

Summary of Toxin Activity Spectrum Results

| Species | DK9.2 $PD_{50}$ (nmol/gm) | 95% CI* (nmol/gm) | DK11 $PD_{50}$ (nmol/gm) | 95% CI (nmol/gm) | DK12 $PD_{50}$ (nmol/gm) | 95% CI (nmol/gm) |
| --- | --- | --- | --- | --- | --- | --- |
| TBW | 0.38 | 0.23–0.61 | 0.71 | 0.39–1.29 | 3.18 | 1.84–5.22 |
| BAW | <1.0 | N/A | <1.5 | N/A | <1.0 | N/A |
| CL | <0.5 | N/A | 0.86 | 0.41–2.0 | <1.0 | N/A |
| ECB | 0.80 | 0.63–1.03 | | | | |
| FAW | 0.93 | 0.62–1.82 | | | | |
| CEW | <0.5 | N/A | | | | |
| SBL | 0.76 | 0.44–1.91 | | | | |
| DBM | <0.2 | N/A | | | | |

*CI = confidence interval (1985). Toxicity to BAW and CL larvae is similar, although these species appear to be more sensitive than TBW to toxin 12. As the principal insecticidal component of *D. canities* venom, DK 9.2 was further tested in a variety of agricultural pests, including the European corn borer (ECB; *Ostrinia nubilalis*), the fall armyworm (FAW; *Spodoptera frugiperda*), the corn earworm (CEW; *Helicoverpa zea*), the soybean looper (SBL; *Pseudoplusia includens*) and the diamondback moth (DBM; *Plutella xylostelia*). All are lepidopteran pests: *S. frugiperda*, *H. zea*, and *P. includens* are in the family Noctuidae, *P. xylostella* is in the family Plutellidae, and *O. nubilalis* is in the family Pyralidae. Assays were performed by the methods described above. In all these species the potency of DK 9.2 was similar to that observed in TBW, indicating that Diguetia toxins are likely to have a broad spectrum of insecticidal activity. This interpretation is further supported by the results of preliminary experiments (see Example 1) with the house fly (*Musca domestica*) and the house cricket (*Acheta domestica*).

Example 3

Purification of *Diguetia canities*, Fraction 11

In a manner similar to that of Example 2, Fraction 11 isolated from *Diguetia canities* whole venom as in Example 1 was further purified by reverse phase liquid chromatography, obtaining one fraction. This fraction was concentrated by lyophilization from the eluant followed by lyophilization from water, leaving a residue, labeled residue 11. This residue was tested for insecticidal activity against tobacco budworm at 5.0 WVE/g as outlined in Example 2.

After 24 hours 80% of the insects treated with residue 11 exhibited paralysis, and after 48 hours 60% of the insects treated with this peptide exhibited paralysis. The control insects appeared normal.

Analysis of this polypeptide by fast atom bombardment mass spectrometry indicated a molecular weight of 6740±2. N-terminal amino acid sequence analysis resulted in a partial amine acid sequence for residue 11 substantially as shown in SEQ ID NO:3, amine acids 1–29. Diguetia toxin DK 11 has a $PD_{50}$ of 0.71 nmol/gm in TBW larvae, and shows similar potency in BAW and CL larvae (Table II).

Example 4

Purification of Diguetia canities, Fraction 12

In a manner similar to that of Example 2, Fraction 12 isolated from Diguetia canities whole venom as in Example 1 was further purified by reverse phase liquid chromatography, obtaining one fraction. This fraction was concentrated by lyophilization from the eluant followed by lyophilization from water, leaving a residue, labeled residue 12. This residue was tested for insecticidal activity against tobacco budworm as outlined in Example 2. After 24 hours 100% of the insects treated with residue 12 exhibited paralysis and after 48 hours 80% of the insects treated with residue 12 exhibited paralysis. The control insects appeared normal.

Analysis of this polypeptide by fast atom bombardment mass spectrometry indicated a molecular weight of 7080±2. N-terminal amine acid sequence analysis resulted in the tentative partial amine acid sequence for residue 12 as shown in SEQ ID NO:5. Diguetia toxin DK 12 has a $PD_{50}$ of 3.18 nmol/gm in TBW larvae but appears to be more effective in BAW and CL larvae ($PD_{50}<1.0$ nmol/gm; Table II).

Example 5

Isolating the coding genes for residue 9.2 and 11 isolated from Diguetia canities venom Spiders were collected from external sources and identified as Diguetia canities. Live spiders were frozen and the cephalothorax removed under liquid nitrogen. RNA was extracted from the cephalothoraces using the protocol of Chomczynski and Sacchi, *Analytical Biochemistry*, 162, 156 (1987). Polyadenylated messenger RNA (mRNA) was purified using oligo d(T) cellulose (Pharmacia LKB, Sweden) chromatography.

Messenger RNA was reverse transcribed to cDNA with murine leukemia virus reverse transcriptase (Bethesda Research Laboratories, Md.) using the manufacturer's protocol. The 20 μl reaction mixture contained the enzyme buffer as supplied in a cDNA synthesis kit (Boehringer Mannheim, Ind.), 50 ng of mRNA, 2 units of RNase H, 30 ng of d(T)Not I primer (Promega, Madison, Wis.), 1 mM each deoxynucleoside triphosphates, and 100 μg of reverse transcriptase. The reaction mixture was incubated for 1 h at 3720 C. and continued for 10 minutes at 42° C. The reaction mixture was ethanol precipitated and resuspended in 20 μl water.

A degenerate primer DNA sequence mixture which could code for amino acid residues I through 8 according to SEQ ID NO:1 was designed using some Drosophila codon preferences to reduce degeneracy. This primer was synthesized by the University of Utah, Howard Hughes Medical Institute contract facility.

Primer directed enzymatic amplification of DNA with a thermostable DNA polymerase was initially described by Saikki et al., *Science*, 239:487 (1988). For our applications, 5 μl of the Diguetia cephalothorax cDNA was used as template in a polymerase chain reaction containing reagents contained in the GeneAmp™ DNA amplification kit (Perkin Elmer Cetus, Calif.). The amplification reaction contained the sense and antisense primers in a 2 μM concentration, 100 μM of each deoxynucleotide triphosphate, and 4 units of the thermostable recombinant Taq I polymerase. The reaction was run in a DNA Thermal Cycler manufactured by Perkin Elmer Cetus. The selective amplification of the gene coding for residue 9.2, from a family of related toxins with similar $NH_2$-terminal amino acid sequences was achieved using stringent annealing temperature (58° C.). These conditions amplified a single DNA which was about 275 base pairs long as determined by agarose gel electrophoresis. Using less stringent annealing conditions, more than five amplified products could be detected by agarose gel electrophoresis with sizes ranging from about 200 to 360 base pairs. These various PCR products obtained at low stringency probably encode polypeptides which are related in amino acid sequence, in approximate size and in insecticidal activity to residue 9.2. Such related polypeptides would be expected to include residues 11 and 12 since the N-terminal sequences of these polypeptides are very similar to each other and to residue 9.2 as shown in SEQ ID NOs: 1, 3 and 5.

The PCR products from both high and low stringency reactions were purified to remove unincorporated primers using a Centricon-100 (Amicon) molecular size separation unit. The retained products were then digested with the restriction enzyme Not I (MBR), Milwaukee, Wis.), which cleaves within the downstream (3' end) primer leaving a sticky end. The vector, pKS (Stratagene, LaJolla, Calif.), was double digested with EcoR V (US Biochemical) and Not I to generate sites specific for directional cloning. Vector and insert were ligated and transformed into compex DH5αF'. Colony lifts were screened with the $^{32}P$ labeled internal probe and candidate colonies were further characterized by sequencing (US Biochemical's Sequenase Version 2.0) of mini-prep DNA using the internal probe as primer.

The entire DNA sequences of the cDNA inserts of two clones are shown in SEQ ID NO:2 and 4. Only the former was obtained in clones derived from the stringent PCR reaction, while both types of cDNA inserts were found in clones obtained from the products of the low stringency PCR reaction. The amino acid sequence of the polypeptide encoded by SEQ ID NO:2 is shown in SEQ ID NO:1. This polypeptide has an N-terminal sequence identical with that determined for residue 9.2. The calculated molecular weight of this polypeptide is 6377.9 Daltons. Assuming that all cysteines in the native polypeptide exists in the form of intramolecular disulfide bonds (cystine), the calculated molecular weight would be 6369.7 Daltons. Therefore, this polypeptide appears to be identical with the polypeptide isolated in residue 9.2 which exhibited a molecular weight of 6371±2 by mass spectrometry. The amino acid sequence of the polypeptide encoded by SEQ ID NO:4 is shown in SEQ ID NO:3. This polypeptide has an N-terminal sequence identical with that determined for residue 11. Therefore, this polypeptide appears to be the same polypeptide isolated in residue 11.

Example 6

Mammalian Toxicity

Whole venom, 5 μl, obtained from *D. canities* as described herein was fatal to mice by intraperitoneal injection (i.p.) in three separate tests. Treated mice were initially indistinguishable from saline controls. About 10 to 15 minutes after injection, treated mice became moderately hyperactive, displaying a characteristic hopping gait; this was followed by a short period of uncoordination, labored breathing and convulsions. Death followed within 2 minutes of the initial onset of symptoms.

Residues 9.2, 11 and 12 were injected intraperitoneally in mice in approximate doses of 4.2, 0.9 and 1.2 mg/kg respectively with no effects seen within 24 hours for all three peptides.

Residue 9.2 was injected into the intracerebral ventricles in four mice (approx. 28 gm) at a dose of approximately 30 µg per animal (approximately 1 mg/kg). No effects were noted at any time up to 48 hours post injection. Another mouse was (i.p.) with approximately 125 µg (4.2 mg/kg) of residue 9.2 and no effects were seen.

To characterize the vertebrate toxicity of this venom, pooled reversed-phase fractions of whole venom were tested in mice (FIG. 1). Fraction 2 comprised the components with tobacco budworm (TBW) activity. At a dose equivalent to 25 ul of whole venom (WVE), intraperitoneal injection of fractions 1 and 2 had no effect; fraction 3 produced the same effects observed with the injection of whole venom. These results suggest a clear disjunction between the insecticidally effective and vertebrate (toxic) activities present in the components of Diguetia canities venom.

Example 7

Electrophysiology Data

Figure 2:
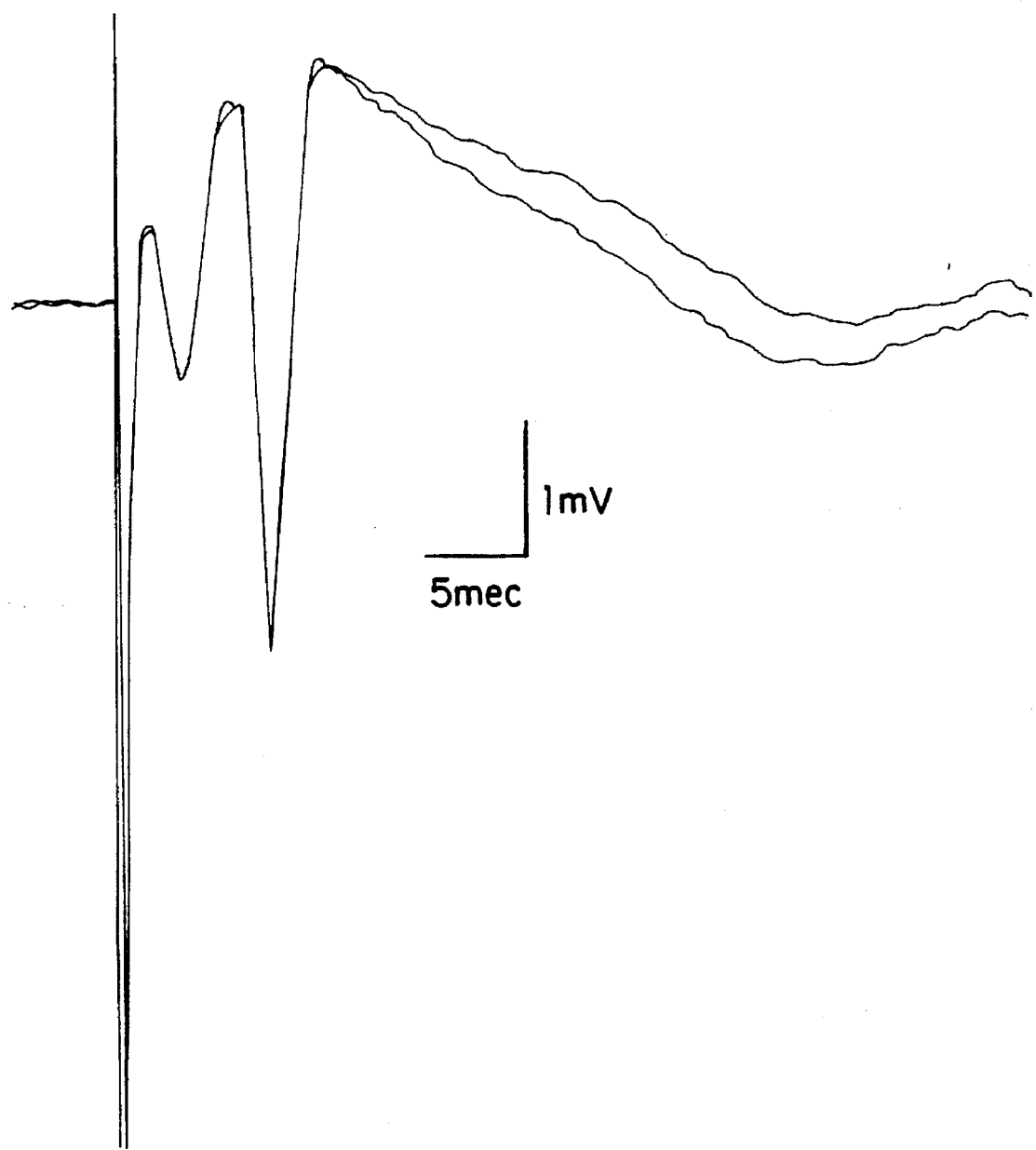
FIG. 2 shows DK 9.2 tested at 1 µM on synaptic transmission (evoked population spike) at the Schaffer collateral-CA 1 pyramidal cell synapse in rat hippocampal slices. The data depicted represent the time-averaged population spike recordings (a) for 5 minutes prior to DK 9.2 addition and (b) during the 15–20 min interval following DK 9.2 addition. These recordings are identical which indicates that, at this concentration, DK 9.2 has no activity in the rat CNS that can be detected in this assay.

DK 9.2 was tested at 1 µM on synaptic transmission (evoked population spike) at the Schaffer collateral-CA 1 pyramidal cell synapse at rat hippocampal slices. The data depicted in FIG. 2 represent the time-averaged population spike recordings (a) for 5 minutes prior to DK 9.2 addition and (b) during the 15–20 min interval following DK 9.2 addition. These recordings can be superimposed, indicating that, at this concentration, DK 9.2 has no activity in the rat CNS that can be detected in this assay. The assay is capable of detecting a variety of effects on various mammalian ion channels and neurotransmitter receptors (T. V. Dunwiddie, *The Use of In Vitro Brain Slices in Neuropharmacology*, in Electrophysiological Techniques in Pharmacology, edited by H. M. Geller, Alan R. Lies, Inc., New York, 1986). In particular, molecules which prevent the inactivation of sodium channels, such as certain scorpion toxins, cause a pronounced broadening of the last phase of the population spike response (Kaneda M, Myama Y, Ikemoto Y and Akaike N., *Scorpion toxin prolongs an inactivation phase of the voltage-dependent sodium current in rat isolated single hippocampal neurons*, Brain Res. 487: 192–195, 1989; Alan L. Mueller, Natural Product Sciences, Inc., unpublished observations). In contrast, DK 9.2 is active in insect preparations (housefly) at 100 times lower concentrations and in a manner which suggests that it prevents the inactivation of insect sodium channels.

Example 8

Upstream cDNA sequences encoding the precursor of DK 9.2

In order to obtain the upstream sequences of the cDNA encoding DK 9.2, an internal oligonucleotide corresponding to nucleic acid residues #159 to 178 on the antisense strand of the DNA sequences presented in SEQ ID NO:2, was synthesized. An Eco RI restriction site is present at the 5' end of this primer. Ten microliters of single stranded venom gland cDNA was tailed at its 3' end with deoxyguanosine residues using the enzyme, terminal deoxynucleotide transferase (Bethesda Research Laboratories). A 20 µl reaction containing 14 units of enzyme and 500 µM of dGTP was incubated at 37° C. for 15 minutes. The sample was ethanol precipitated and resuspended in 20 µl $H_2O$.

DNA sequences upstream of the gene specific primer were amplified using an anchored PCR technique similar to that used for the downstream/mature toxin cDNA sequnces. The amplification reaction contained the sense, (a d(C) tailed primer), and antisense primers in a 2 µM concentration, 100 µM of each deoxynucleotide triphosphate, and 4 units of the thermostable recombinant Taq polymerase. The temperature profile was as follows: 2 min at 94° C., 2 min at 37° C., 1 min at 37° C. This cycle was repeated twice and the program then switched to an identical profile incorporating an elevated annealing temperature of 54° C. at the second step. This cycle was repeated 32 times.

Anchored PCR yielded a 380bp fragment as evidenced on a 4% agarose gel in the presence of ethidium bromide. This reaction product was filled in at the ends using the large (Klenow) fragment of *E. coli* DNA Polymerase I (Molecular Biology Resources, Madison, Wis.), and precipitated by the addition of ethanol. The product was resuspended and digested with the restriction enzyme, Eco RI. The digested fragment was kinated in the presence of 1 mM ATP by the enzyme T4 Kinase and subsequently ligated to Eco RI and Eco RV digested pBluescriptsKS vector. Subclones were analyzed by double-stranded DNA sequencing using Sequenase 2.0 (USB).

Translation of the cDNA sequences contained in the region upstream to the mature peptide toxin revealed DK 9..2 to be synthesized as a precursor protein. The upstream cDNA sequence presented in SEQ ID NO:6. The encoded precursor protein is comprised of a signal sequence and propeptide region (SEQ ID NO:7) which are removed to yield the mature peptide toxin which is isolatable from spider venom. It is speculated that the signal and propeptide sequences are necessary for the production and secretion of DK 9.2 in the spider.

Example 9

Recombinant Baculovirus Construction

A lepidopteran signal sequence (Jones et al., Molecular Cloning Regulation and Complete Sequence of a Hemocyanin-Related Juvenile Hormone-Supressible Protein From Insect Hemolymphs, *J. Biol. Chem.* 265:8596 (1990)), was constructed from two synthetic oligonucleotides using the method of Rossi, et al. (*J. Biol. Chem.* 257:9226 (1982)). Two 48 mers were purified by ion exchange chromatography. These two oligonucleotides share eleven base pairs of complementary sequence at their 3' termini. When the sequences were annealed in the presence of the four deoxy-ribonucleoside triphosphates and the Klenow fragment of DNA polymerase I, a double-stranded product was synthesized. Reaction products were purified using hydroxylapatite chromatography and the double-stranded DNA molecules were digested with Aat II, the restriction enzymes appropriate for inserting this sequence upstream of DK 9.2 cDNA cloned into pKS-DK9c. Subclones were screened for the insertion of the signal sequence and evaluated by DNA sequencing.

Figure 3:
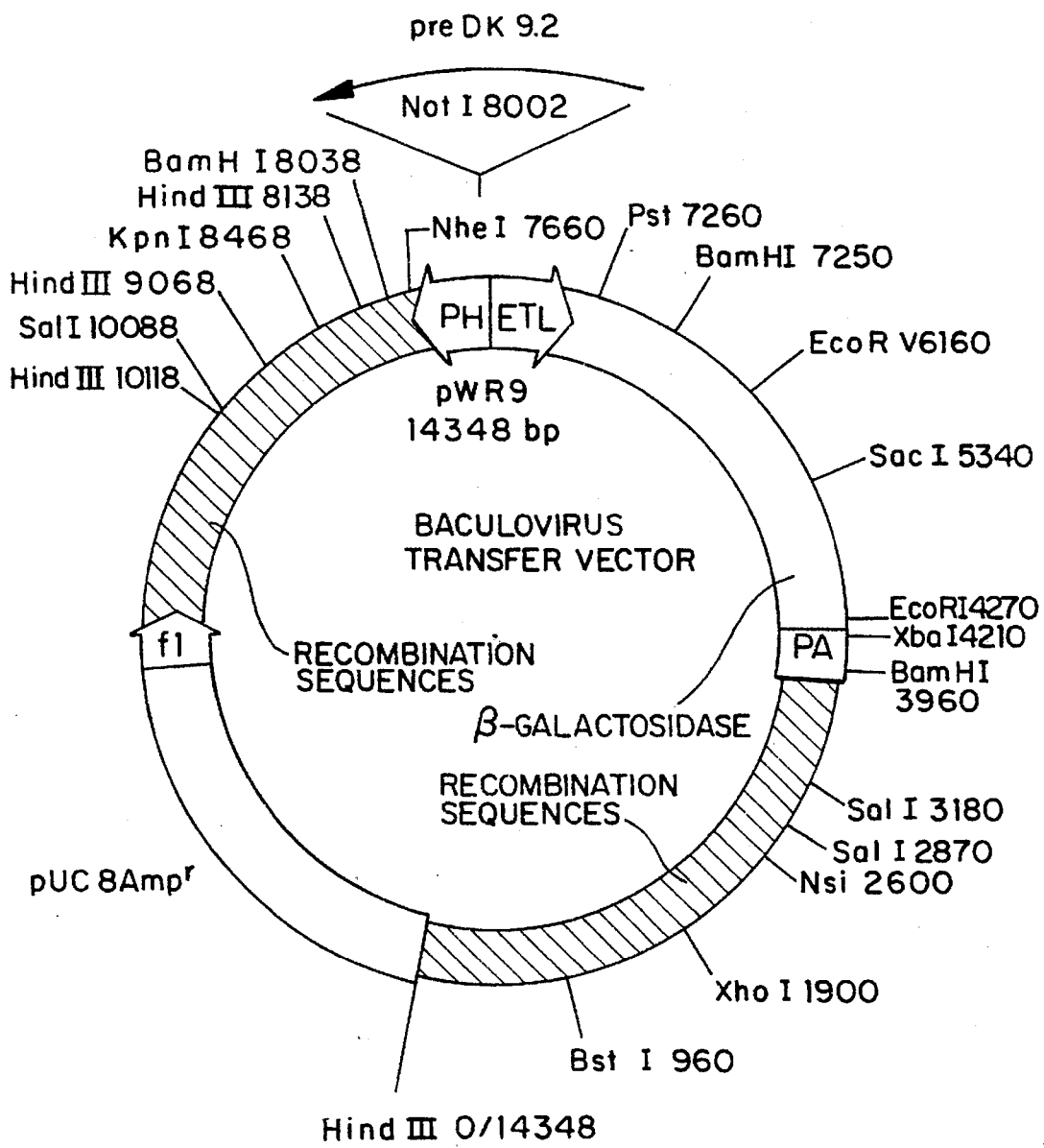
FIG. 3 is a map of $_p$WR9, a baculovirus transfer vector carrying the gene encoding preDK9.2.

DNA sequencing confirmed an in-frame fusion between the two cDNA sequences. The entire synthetic gene construct was excised and adapted for cloning into the NheI site of pBlueBac, a baculovirus transfer vector [Vialard, J., et al., J. Virology 64:3–50 (1990)]. Subclones were sequenced to confirm the correct insertion of the construct. DNA sequencing of plasmid WR9 confirmed the insertion of the synthesized "caterspider" gene (preDK 9.2) in the baculovirus transfer vector pBlueBac (FIG. 3). The use of the pBlueBac vector expedites the screening process as insertion of our recombinant gene into the baculovirus genome is accompanied by co-expression of β-galactosidase and detectable by a color change when grown on indicating media.

Recombinant baculoviruses encoding preDK 9.2 were produced by transfection of Spodoptera frugiperda strain Sf9 (ATCC# CRL1711) cells with a mixture of 1 μg AcMNPV viral DNA and 2 μg plasmid DNA using the protocol of Summers and Smith (in "A Manual of Methods for Baculovirus Vectors and Insect Cell Culture Procedures", Texas Agricultural Experiment Bulletin No. 1555, 1988). Four days post-transfection, dilutions of the cell supernatant were plaqued on 100 mm plates seeded with $5 \times 10^6$ Sf9 cells and covered with agarose containing Bluo-gal (Gibso BRL, Gaithersburg, Md.) as substrate. Within 5 to 6 days, recombinants were detectable by their pale blue color. Plaques were picked using a pasteur pipet and eluted in 1 ml of media. This eluent was used to re-infect Sf9 cells seeded into a T-25 flask. Three days post-infection a small volume of supernatant was collected from six different isolates and used to prepare viral DNA. PCR amplification using viral specific primers from the region surrounding the polyhedrin gene confirmed that five of the six viral isolates contained an appropriately sized insert and lacked any wild-type contamination. Titered stocks of the recombinant viruses were then prepared for in vivo and in vitro testing.

Example 10

Biological Activity of Recombinant DK 9.2:

Biological activity of recombinant residue 9.2 (DK 9.2), purified from serum-containing tissue culture medium, was tested in last instar TBW larvae. Doses were calculated on the basis of the $A_{280}$ of the test solution. At a dose of 16 μg/g, the recombinant material caused pronounced muscle spasms within 2 hours of injection. Half (3 of 6) of these larvae were paralyzed and severely contracted after 48 hours, while the other 3 larvae were still displaying slight to moderate muscle spasms. A dose of 9 μg/g also paralyzed 3 of 6 larvae, while a dose of 5.2 μg/g paralyzed 2 of 6 larvae. The results confirm that recombinant DK 9.2 is biologically active.

Example 11

Recombinant Baculovirus—In vivo testing

A. Biological activity of DK 9.2 recombinant nuclear polyhedrosis virus (vACDK9.2).

1) Titration of viral preparations.

Viral stocks were titered by the plaque assay method (Luria et al., "General Virology", 1978, pp. 21–32; John Wiley and Sons, New York). Titers were expressed in terms of plaque forming units (PFU) per unit volume, whereas doses were expressed as PFU/larva. One PFU is the functional equivalent of one mature virion (virus) in a preparation wherein every virion is capable of successfully infecting one host cell (Luria et al., ibid). For example, $10^3$ host cells could be infected by each microliter of viral preparation containing $10^6$ PFU/ml (i.e., $10^3$ PFU/μl ).

2) Bioassays.

The biological activity of the DK 9.2 recombinant nuclear polyhedrosis virus (rNPV), vAcDK9.2, was tested in a series of dose response assays. In these assays, TBW larvae (mean mass approximately 250 mg) were injected with various doses of vAcDK9.2 in tissue culture medium or with tissue culture medium alone (n=10). As in the toxin injection experiments described in Example 1, treated larvae were held in individual containers with a supply of food and observed periodically. The combined results of two such viral injection assays are illustrated in Table III. At doses of 5000 PFU/larva and greater, the typical symptoms of DK 9.2 toxicity (muscle tremors and spasms) began appearing at about 24 hours post-infection, and at least half the test insects were incapacitated (i.e., paralyzed or partially paralyzed) within 48 hours. The lowest dose tested, 50 PFU/larva, induced tremors and spasms within 48 hours and incapacitated at least 70% of the larvae in 96 to 120 hours.

B. Biological activity of vAcDK 9.2 in comparison with wild type NPV.

Further studies were conducted to determine the efficacy of vAcDK 9.2 in comparison with its parental wild type virus, Autographa californica NPV (wt-AcMNPV). The objective of these assays was to determine whether larvae infected with vAcDK 9.2 were incapacitated in less time than larvae infected with an identical dose of wt-AcMNPV.

1) Injection Assays.

The biological activities of vAcDK 9.2 and wt-AcMNPV were compared in a series of injection assays. Last instar tobacco budworm (Heliothis virescens) larvae, cabbage looper (Trichoplusia ni) larvae, and beet armyworm (Spodoptera exigua) larvae were injected with $5 \times 10^5$ PFU/larva of vAcDK 9.2 or wt-AcMNPV; control larvae were injected with tissue culture medium. The results, summarized in Table IV, demonstrate that vAcDK 9.2 is substantially more effective than wt-AcMNPV in all three species.

The efficacy of vAcDK 9.2 in comparison with wt-AcMNPV was further tested in TBW, BAW, CL, SBL, FAW, ECB, and CEW larvae. Larvae (ten per treatment) were injected with vAcDK 9.2 or wt-AcMNPV at a dose of $10^6$ PFU/larva, or with tissue culture medium. The results (Table V) confirm that vAcDK 9.2 is substantially more effective than wt-AcMNPV in all of these insects (no mortality was noted in any control group). Even in species that appeared to be marginal hosts for the viruses (FAW, CEW, ECB), vAcDK 9.2 acted 50 to 70 percent faster than wt-AcMNPV. In all species, larvae treated with vAcDK 9.2 developed the typical symptoms of Diguetia toxin poisoning (continuous, severe muscle spasms, contraction of the body in all dimensions, etc.); these effects were never present in control larvae or larvae treated with wt-AcMNPV. These results clearly indicate that vAcDK 9.2 possesses essentially the same patterns of infectivity as wt-AcMNPV, and that the cells of susceptible species are capable of expressing effective amounts of the recombinant toxin.

2) Feeding Assays.

In order to test the activity of vAcDK 9.2 by ingestion, it was necessary to produce this polyhedrin-negative (pol−) recombinant in an orally infective form. This was accomplished by co-occlusion of vAcDK 9.2 with wt-AcMNPV, using methods reported by other workers for producing orally infective pol-recombinant NPVs (e.g., Kuroda et al., 1989, J. Virology 63(4): 1677–1685, and Price et al., 1989, Proc Natl. Acad. Sci. 86:1453–1456). SF-9 cells were simultaneously infected with vAcDK9.2 and wt-AcMNPV at multiplicities of infection (MOI) of 10 and 2, respectively.

At the same time, a second group of SF-9 cells was infected with wt-AcMNPV alone (MOI=2). Five days after infection, inclusion bodies were harvested by cell disruption and differential centrifugation (e.g., Wood, 1980, Virology 104:392–399). Inclusion bodies were counted on a hemacytometer. Cells which were co-infected with vAcDK 9.2 and wt-AcMNPV produced fewer and smaller inclusion bodies than cells infected with wt-AcMNPV alone. The yield of polyhedral inclusion bodies (PIB) from the mixed infection was 4.6 PIB/cell, while the yield from the pure wt-AcMNPV infection was 33.3 PIB/cell.

Figure 4:
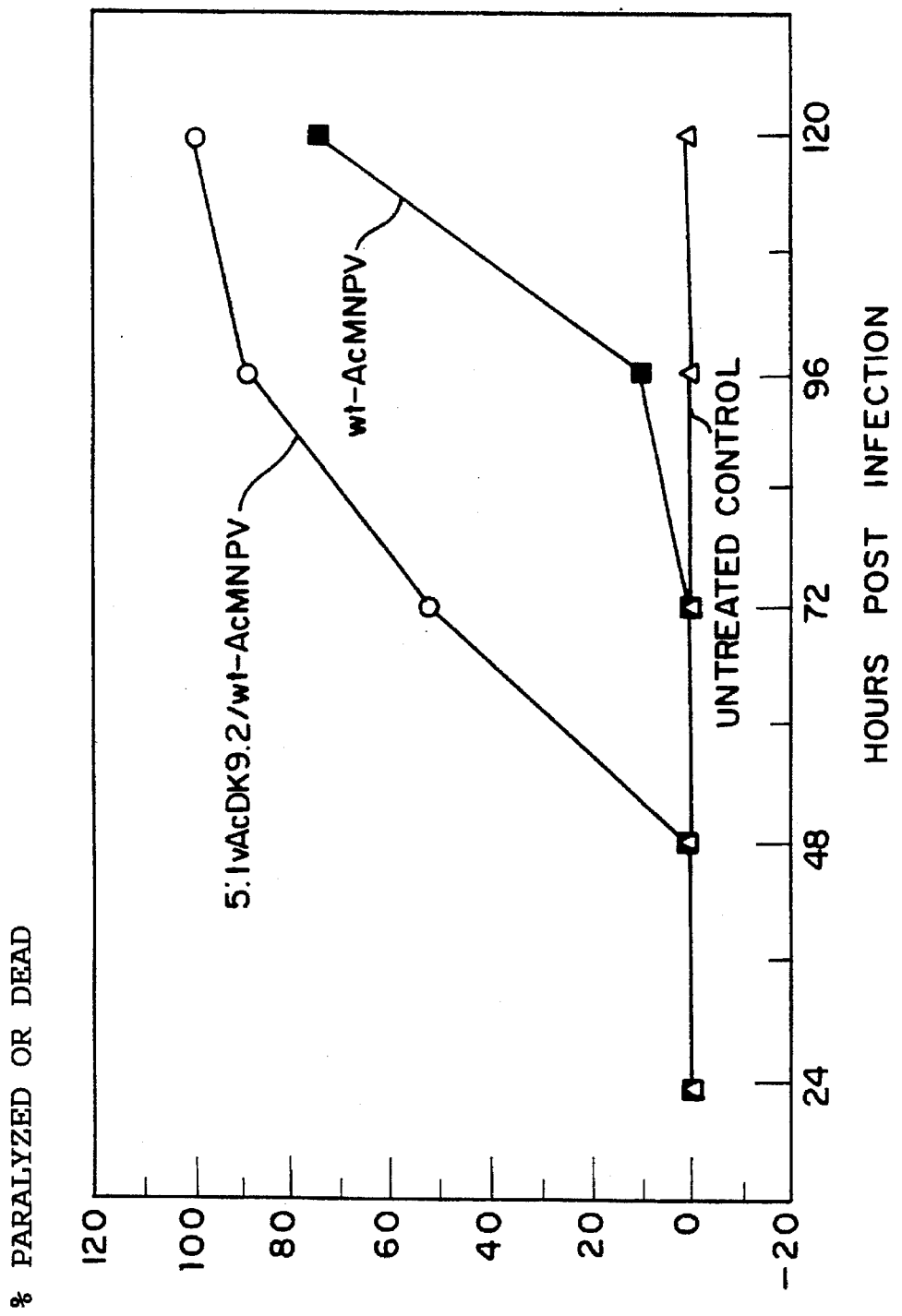
FIG. 4 is a continuous viral feeding assay in neonate tobacco budworm (100,000 PIB/gm diet).

To assess the biological activity of the co-occluded vAcDK 9.2 in comparison with that of wt-AcMNPV, a diet incorporation assay was used. Mixed or wild-type PIB were incorporated into a non-agar based insect diet at a concentration of $10^5$ PIB/gm diet. The diet was dispensed into small containers, which were subsequently infested with neonate TBW larvae (1 per container, n=20). Control larvae were given identical amounts of untreated diet. The larvae were allowed to feed ad libitum, and were observed periodically for the development of symptoms. Results are shown in FIG. 4. No effects were noted for the first 48 hours, but after 72 hours more than 50% of the larvae which had fed on the mixed PIB were paralyzed. The wild type virus had no effect at this time. After 96 hours, more than 90% of the recombinant-treated larvae were paralyzed, whereas only 10% of the wild-type treated larvae were dead or moribund. After 120 hours, 100% of the recombinant-treated larvae were dead or moribund, as compared to 75% of the larvae treated with wt-AcMNPV. Thus, in a feeding assay, as in the injection assays, vAcDK 9.2 treated larvae were incapacitated in a significantly shorter time than larvae treated with wt-AcMNPV.

Figure 5:
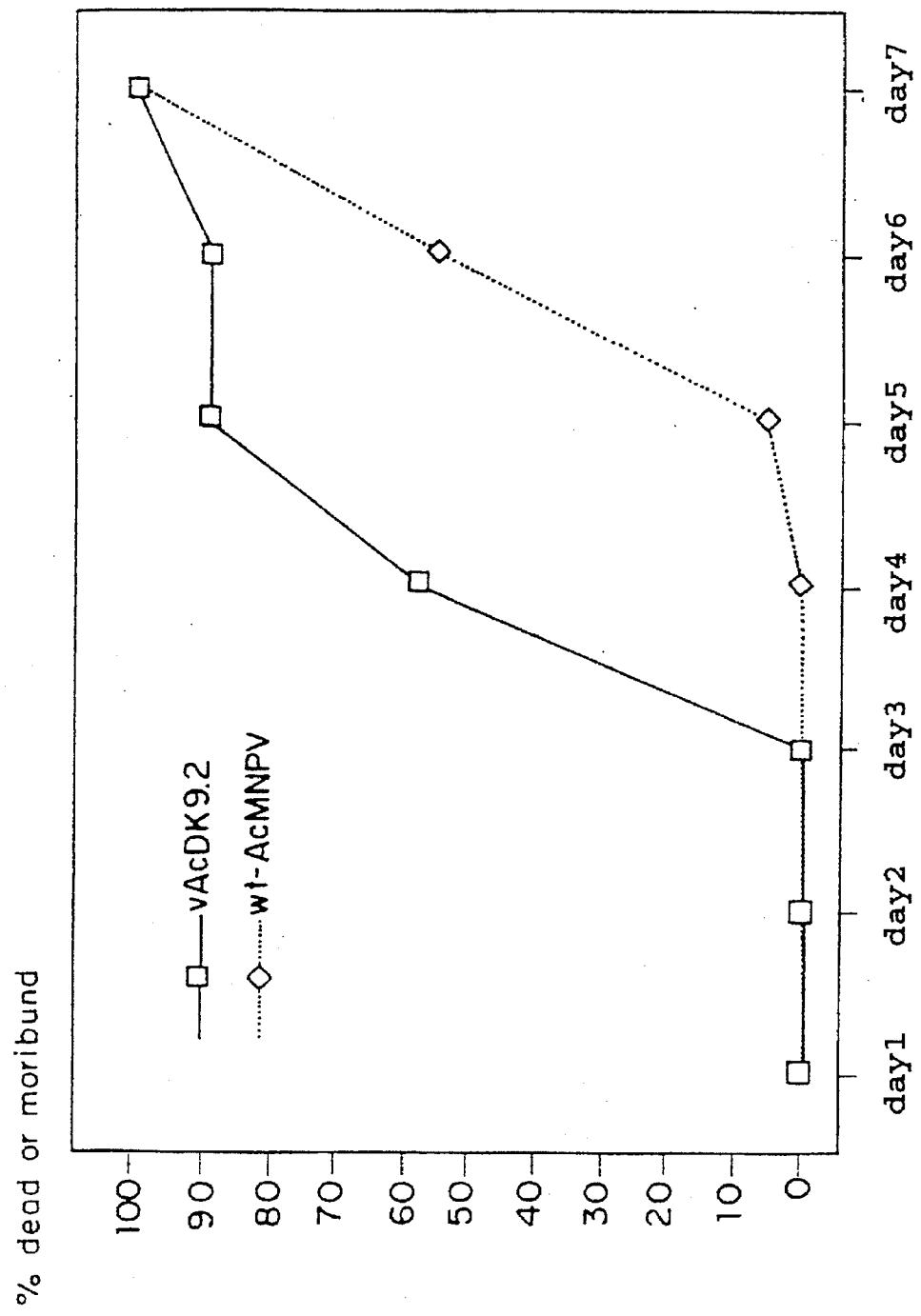
FIG. 5 is a second continuous viral feeding assay in neonate tobacco budworm (100,000 PIB/gm diet).

This feeding assay was repeated with a second batch of co-occluded vAcDK 9.2, prepared by an analogous procedure. As described above, PIB were produced in SF-9 cells and the co-infection ratio of recombinant to wild type viruses was 5:1. TBW larvae (n=20), held in individual containers, were allowed to feed ad libitum on artificial diet containing $10^5$ PIB/gm of the wild type or the co-occluded recombinant virus. Control larvae were given untreated diet. As before, time zero was considered to be the moment when the larvae were introduced into the containers with the treated diet. The results of this assay were similar to the initial feeding assay: more than 50% of the recombinant-treated larvae were paralyzed within 96 hours, and the recombinant incapacitated $\geq 90\%$ of the insects roughly 48 hours earlier than the wild type virus (FIG. 5).

Figure 6:
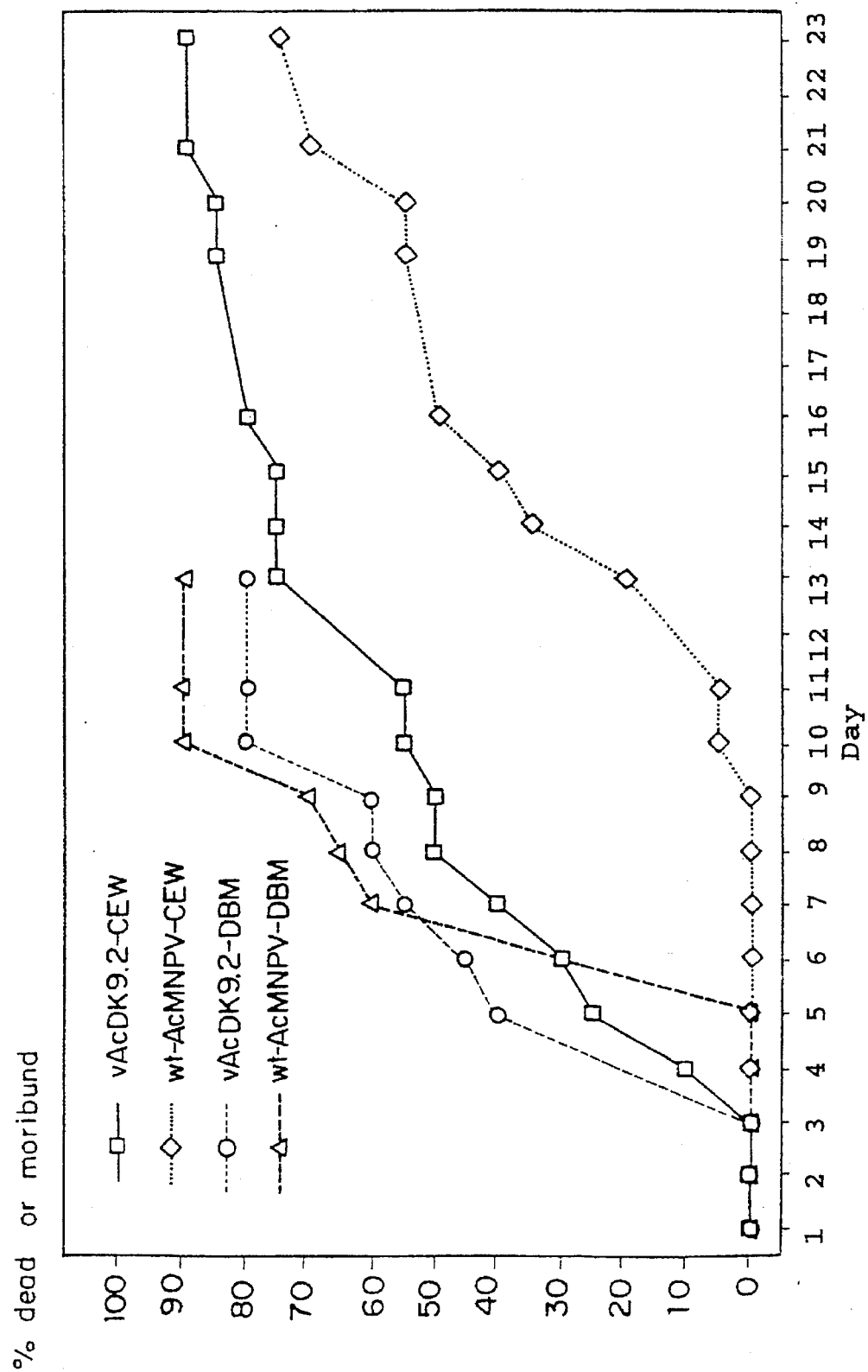
FIG. 6 is a continuous viral feeding assay in neonate corn earworm and second instar diamondback moth larvae (1,000,000 PIB/gm diet).

Larval feeding assays were also conducted with neonate CEW larvae and second instar DBM larvae. The protocol was identical to that used in the TBW feeding assays, except that the diet contained $10^6$ PIB/gm rather than $10^5$ PIB/gm. In both species, the co-occluded recombinant was more effective than the wild type virus (FIG. 6). Taken with the injection assay data, these results strongly suggest that vAcDK 9.2 is likely to have enhanced activity, relative to wt-AcMNPV, in any species of insect that is susceptible to the virus.

TABLE III

Dose-Response Assays in TBW with vAcDK9.2
% Paralysis

| DOSE (PFU/larva) | 24 HR | 48 HR | 72 HR | 96 HR | 120 HR |
|---|---|---|---|---|---|
| $5.1 \times 10^5$ | 0 | 80 | 100 | 100 | 100 |
| $5.1 \times 10^4$ | 0 | 35 | 95 | 100 | 100 |
| $5.1 \times 10^3$ | 0 | 25 | 75 | 90 | 100 |
| $5.1 \times 10^2$ | 0 | 0 | 55 | 85 | 100 |
| $5.1 \times 10^1$ | 0 | 0 | 20 | 65 | 95 |
| CONTROL | 0 | 0 | 0 | 0 | 0 |

TABLE IV

Comparison of vAcDK9.2 and wt-AcMNPV by Injection[1] in Tobacco Budworm (TBW), Cabbage Looper (CL), and Beet Armyworm (BAW) Larvae

| TREATMENT | SPECIES | 24 HR | 48 HR | 72 HR | 96 HR | 120 HR | 168 HR |
|---|---|---|---|---|---|---|---|
| vAcDK9.2 | TBW[2] | 0 | 0 | 100 | 100 | 100 | 100 |
| wt-AcMNPV | TBW | 0[3] | 0 | 0 | 0 | 0 | 0[4] |
| Control | TBW | 0 | 0 | 0 | 0 | 0 | 0 |
| vAcDK9.2 | CL[5] | 0 | 100 | 100 | 100 | 100 | N/A |
| wt-AcMNPV | CL | 0 | 0 | 0 | 0 | 100 | N/A |
| Control | CL | 0 | 0 | 0 | 0 | 0 | N/A |
| vAcDK9.2 | BAW[6] | 0 | 70 | 90 | 100 | 100 | 100 |
| wt-AcMNPV | BAW | 0 | 0 | 0 | 0 | 0 | 100 |
| Control | BAW | 0 | 0 | 0 | 0 | 0 | 30 |

[1]Viruses were injected at $5 \times 10^5$ PFU/larva; controls were injected with identical volumes of tissue culture medium.
[2]n = 8; mean mass approximately 300 mg per larva.
[3]2 of 8 larvae apparently died from physical trauma due to the injection and were excluded from further analysis.
[4]Mortality from wt-AcMNPV was 100% on day 9.
[5]n = 10; mean mass approximately 165 mg per larva.
[6]n = 20 for vAcDk9.2; n = 10 for wt-AcMNPV and controls; mean mass approx. 200 mg per larva.

TABLE V

Relative Efficacy of vAcDK9.2 and wt-AcMNPV by Injection in Various Species at $10^6$ PFU/larvae (n = 10)

| Species | Initial Mortality Time (wt) | Ultimate Mortality Time (wt) | Initial Paralysis and Time (Recombinant) | Ultimate Paralysis and Time (Recombinant) | % Reduction in Time to Initial Effects | % Reduction in Time to Peak Mortality* |
|---|---|---|---|---|---|---|
| BAW | 40% day 6 | 100% day 8 | 20% day 2 | 100% day 4 | 66% | 50% |
| CL | 20% day 4 | 100% day 6 | 100% day 2 | 100% day 2 | 50% | 66% |
| TBW | 60% day 7 | 100% day 9 | 70% day 2 | 100% day 3 | 71% | 66% |
| SBL | 20% day 6 | 100% day 7 | 100% day 3 | 100% day 3 | 50% | 57% |
| FAW | 40% day 8 | 100% day 10 | 20% day 3 | 100% day 4 | 62.5% | 60% |
| ECB | 40% day 15 | 60% day 17 | 30% day 5 | 100% day 15 | 69% | >50% |
| CEW** | 10% day 6 | 60% day 12 | 40% day 6 | 80% day 7 | 4-fold greater incapacitation on same day | 59% |

*This percentage is the reduction in time required for the recombinant virus to cause the peak level of mortality or morbundity caused by the wild type virus. When both viruses ultimately caused 100% mortality, the times required for this were directly compared. In several cases, however, the recombinant virus cause a higher percentage of mortality than the wild type virus. When this was the case (e.g., for the European corn borer), the time required for the wild type virus to cause its peak mortality (60% in this case) was compared with the time required for the recombinant virus to cause the same (60%) level of mortality or morbundity.
**CEW larvae were given a dose of $10^5$ PFU/larva.

Example 12

Promoter for the gene encoding DK 9.2

To access the control elements of the gene encoding DK 9.2, a genomic library was made. DNA was prepared from spiders using a protocol adapted from Herrmann and Frischauf (in "Methods in Enzymology", Vol. 152, Academic Press, Inc. 1987, pp. 180–183). The DNA was partially digested with Sau 3A and fractionated by centrifugation in a 10%–38% sucrose density gradient at 25,000 rpm for 16 h with a TLS-55 rotor (Beckman Co., Ltd). Pooled DNA fractions of 35–45 kb were prepared for insertion into an Xho I digested cosmid vector using the partial fill-in method. One-quarter of the ligation mixture was packaged into phage particles using Gigapak gold™ (Stratagene, LaJolla, Calif.) and after transformation the equivalent of over $3\times10^9$ bp of spider DNA was obtained. The library was plated onto twenty-five 150 mm petri plates and lifted onto nylon filters for probing with radiolabeled DNA.

Colony lifts of the Diquetia genomic library were screened in series with the radiolabeled cDNA encoding DK 9.2, and end-labeled origonucleotides encoding the amino-terminus, the carboxyterminus and an internal probe. One cosmid, cDK2, hybridized with all of the probes. A southern blot of Eco R1 digested cosmid DNA indicated a 3.0 kb fragment to hybridize with both the internal and C-terminal probes. Double stranded sequencing of the cosmid cDK2 using the three primers identified above confirmed the isolation of the gene for DK 9.2 and suggested the possibility that another (or other) genes from this family may reside on the same contiguous piece of DNA, as the amino terminal oligonucleotide (which has a high degree of homology to all the Diguetia insecticidally effective peptides), primes at multiple sites on the cosmid DNA.

To access the promoter region of the gene for DK9.2 we had an oligonucleotide synthesized corresponding to the pre/signal sequence on the sense strand. PCR amplification between this primer and another of our gene-specific primers has mapped the signal sequence to be more than 3,000 bp upstream of the amino terminal exon. A primer on the antisense strand was then used to sequence the genomic DNA in the region directly upstream to the 5' end of the cDNA encoding the signal peptide.

DNA sequencing upstream of the signal sequence on the genomic DNA suggested another intron at bp - 11 from the initiation methionine codon. An oligonucleotide primer corresponding to the 5' region of the precursor DK 9.2 cDNA was synthesized and used to prime a PCR reaction to determine how large the intervening sequence is between the transcriptional and translational start sites. A 1,000 base pair amplification product confirmed the presence of the intron and provided an estimate of its size. DNA sequencing of the genomic DNA upstream to the transcriptional start (assumed to be equivalent to the 5' end of the cDNA), does indicate the presence of a promoter. The DNA sequence of the promoter region is presented in SEQ ID NO: 8. This putative promoter contains many of the essential control signals that are generally present in other eucaryotic promoters in the region directly upstream of the translational start site. This promoter or sections of this promoter can be used for the transcription/translation of other eucaryotic genes in bacteria, viruses, plants or animals.

Example 13

Neurophysiologic studies related to the mode of action of DE9.2

Neurophysiological studies were undertaken to elucidate the mode of action of DK 9.2. Recordings from maggot neuromuscular Junction and peripheral nerve show that DK 9.2 induces repetitive burst discharges in nerves that are sensitive to block by tetrodotoxin. Thus, the site of action of this toxin is probably the voltage-sensitive sodium channel of nerve membrane. Additional studies showed that DK 9.2 consistently excites peripheral nerves at a threshold concentration of 10 nM. In addition, it is at least 50 times as potent as mammal toxin 4 of the scorpion *Leiurus quinquestriatus.*

The experimental animals used in this study were third instar larvae of the house fly, *Musca domestica.* Larvae were immobilized with insect pins, and opened dorsally by a medial saggital incision. The body was pinned out flat, and the viscera removed to expose the body wall musculature. The peripheral nerves were severed where they exit the brain and the brain was removed. The preparation was flooded with an insect saline composed of (mM): NaCl (140), KCl (5), $CaCl_2$ (0.75), $MgCl_2$ (4), $NaHCO_3$ (5) and HEPES (5) pH=7.2

A stimulating suction electrode was attached to any convenient nerve trunk to record neuromuscular transmission. The threshold for stimulation was slowly raised until a contracting fiber of muscle 6 or 7 was observed. Then, this fiber was impaled with a recording intracellular microelectrode connected to an intracellular preamplifier used to monitor Excitatory Post Synaptic Potentials (EPSP) in response to nerve stimulation.

For recording ascending electrical activity in peripheral nerve fibers, the suction electrode was attached to an AC preamplifier. Signals were amplified 100-fold and the output filtered at 0.3 and 1 kHz. All recordings were digitized on a MacLab computerized instrumentation system for display and analysis.

Initial experiments on the action of DK 9.2 utilized the neuromuscular junction preparation. A single stimulus applied to the peripheral nerve resulted in a single EPSP in the body wall muscle. In the presence of DK 9.2, a single stimulus resulted in a high frequency discharge of EPSP. In addition to stimulus-evoked discharges, spontaneous burst discharges also appeared and they persisted for several minutes. The duration of a burst was usually over I second, and the frequency of EPSPs during a burst was >30 Hz. The presence of burst discharges caused vigorous contraction in the bodywall musculature, which made it difficult to maintain intracellular recordings because the electrode was ejected from the muscle during a burst-initiated contraction. Accordingly, most experiments were performed in saline containing a high concentration of sucrose (300 mM) which suppresses contraction, but leaves electrical activity unaffected. Similar results were obtained using either normal or high sucrose salines.

Figure 7A:
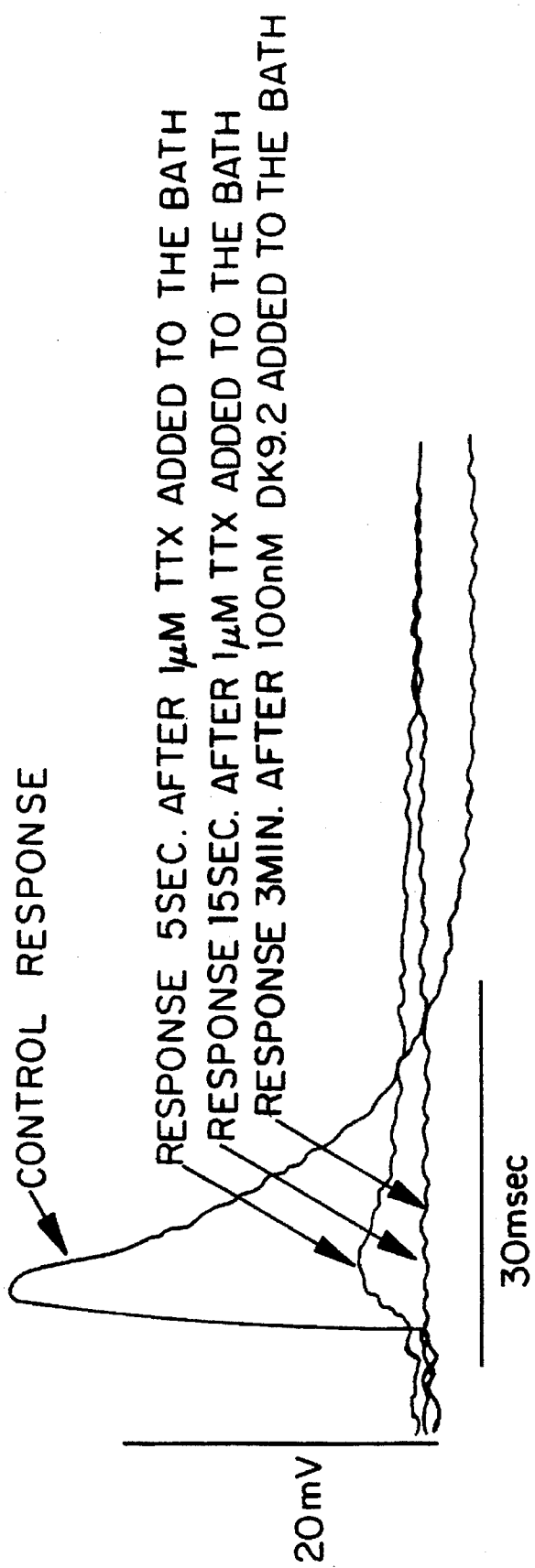
FIGS. 7A and 7B depicts the ability of TTX to prevent or reverse DK 9.2-induced bursting.
Figure 7B:
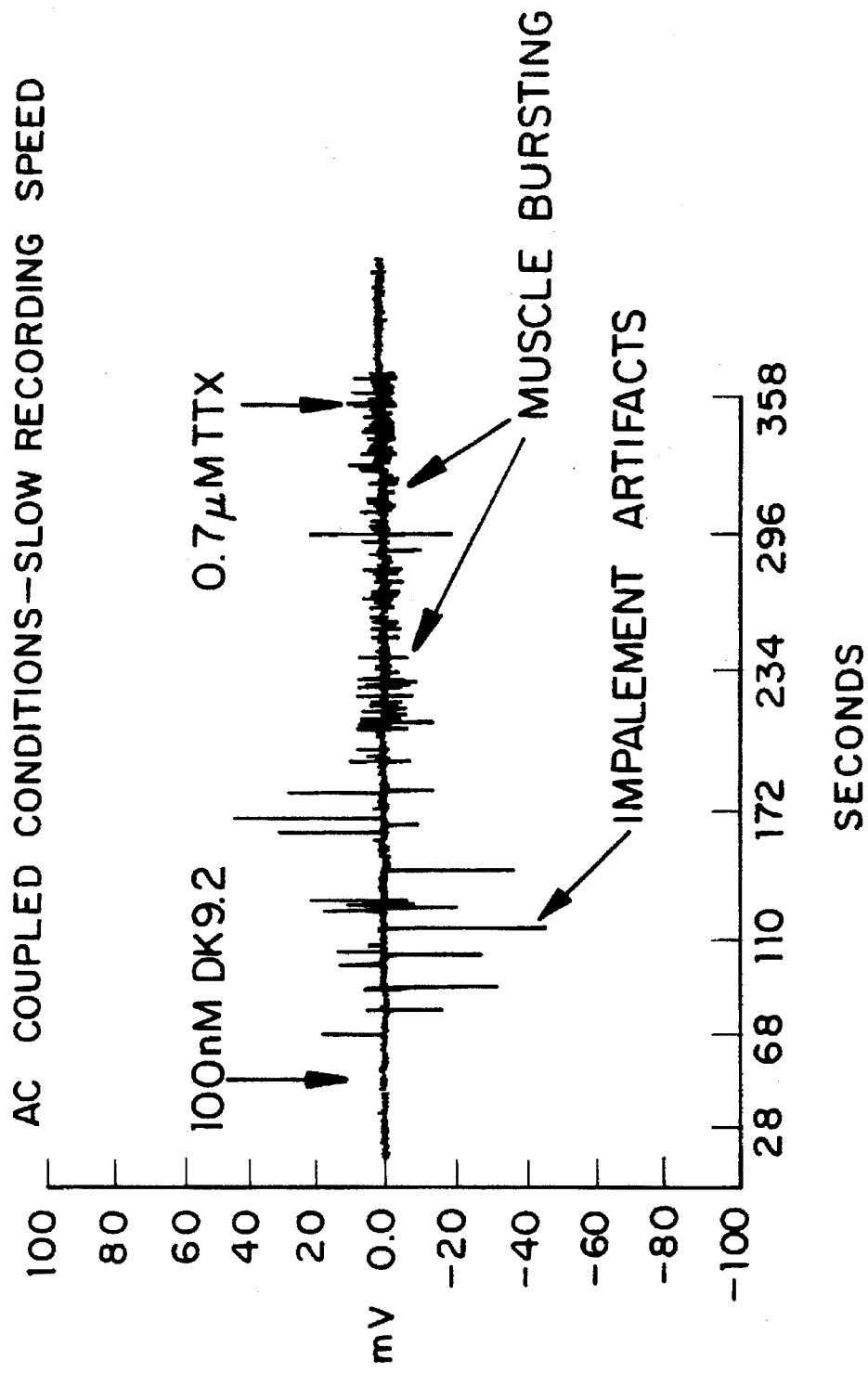

The burst discharges observed after DK 9.2 treatment were similar to those observed in the presence of scorpion α toxins, proteins which are known to interact with the voltage-sensitive sodium channels of nerve membranes. Thus, the burst discharges should be blocked by the specific sodium channel blocker tetrodotoxin (TTX). The ability of TTX to prevent or reverse DK 9.2-induced bursting is shown in FIGS. 7A and 7B. In FIG. 7A, the EPSP was rapidly blocked by 1 µM TTX, which rendered the preparation insensitive to subsequent treatment with 100 nM DK 9.2. A similar experiment is shown in FIG. 7B, where bursting is induced by DK 9.2 and reversed by subsequent application of TTX. In this experiment, the onset of bursting dislodged the electrode from the muscle, resulting in impalement artifacts when an attempt was made to reestablish the recording. Once a suitable recording site was found, bursting was monitored for about 2 min., and the preparation showed cessation of activity within seconds after TTX treatment.

In order to circumvent the problems associated with intracellular recording from contracting muscle, the above experiments were repeated using extracellular recordings from maggot peripheral nerves. These recordings are composed of ascending sensory nerve activity, along with spontaneous antidromic activation of motor fibers. At 70 nM, DK 9.2 causes an increase in nerve discharge that is unaffected by subsequent treatment with saline, but is rapidly blocked by 0.4 µM TTX. In addition, application of TTX before DK 9.2 prevents the appearance of bursting.

Additional studies were undertaken to determine the sensitivity of insect nerves to DK 9.2, and to compare its potency with that of a standard scorpion toxin. DK 9.2 was tested on the peripheral nerve preparation starting at 1 nM, and increasing the concentration every five minutes or so until an increase in activity was observed. In this preparation, 1 nM and 5 nM DK 9.2 were inactive, but 10 nM induced activity in the preparation after a short delay. Results from five nerve preparations used to determine the effective threshold concentration of DK 9.2 on insect nerve are summarized in Table VI.

TABLE VI

| Concentration | Number of Treatments | Number Responding | % Response |
| --- | --- | --- | --- |
| 1 nM | 2 | 0 | 0 |
| 2 nM | 1 | 0 | 0 |
| 5 nM | 3 | 1 | 33 |
| 10 nM | 3 | 3 | 100 |

The last group of experiments determined, in a similar way, the sensitivity of insect nerve to toxin 4 of the scorpion Leiurus quinquestriatus (LqTX 4). Preparations (n=4) were exposed to concentrations of LqTX 4 of up to 500 nM with no effect. This finding is consistent with previous studies, which found that LqTX 4 is specific for mammalian sodium channels. Subsequent challenge of these preparations with DK 9.2 required 10–30nM to get a response. The slight elevation of the effective threshold concentration of DK 9.2 is perhaps due to a weak blocking action by the inactive LqTX 4. These experiments demonstrate that DK 9.2 is at least 50-fold more active than LqTX 4 on insect nerves.

Example 14

Purification of Recombinant Diguetia Toxin 9.2 (rDK9.2) from Insects Infected with vAcDK9.2

Tobacco budworm and cabbage looper larvae were injected with vAcDK9.2 at a dose of $5.1 \times 10^5$ PFU/larva (n=10). After 96 hours, the larvae were ground in 50 mM sodium acetate, pH 2.5 (approximately 2 ml/larva) with an Omni homogenizer. The homogenate was spun at top speed in a clinical centrifuge, and the supernatant was filtered through a 0.2 µm syringe filter. After filtration, 5 ml of the supernatant were loaded onto a 4.6×150 mm HEMA-Bio S column equilibrated in 50mM sodium acetate+150mM sodium chloride, pH 4.0. The column was pumped at 1 ml/min. for 10 minutes in this buffer. A gradient of 15% B to 100% B was then passed through the column over a period of 50 minutes (A=50mM sodium acetate pH 4.0, B=50 mM sodium acetate plus 1M sodium chloride, pH 4.0). The rDK9.2 eluted at approximately 36 minutes. The fractions containing rDK9.2 were loaded onto a 4.6×250 mm Vydac C-18 column equilibrated in 15% B solvent (A=0.1% TFA, B=0.1% TFA in acetonitrile). After 2 minutes at 1 ml/min with this solvent, a gradient was run from 15% B to 100% B over 85 minutes. The fractions containing rDK9.2, as detected by immunoassay, eluted at approximately 23 minutes. The yield of rDK9.2 was 1–3 ug/larva from cabbage loopers and 10–20 ug/larva from tobacco budworms. These results confirm the feasibility of producing biologically active rDK9.2 in vivo by infecting susceptible hosts with vAcDK9.2.

Example 15

Antisera preparation

Rabbits were inoculated with 3 sequential 500 µg doses of a pooled reversed-phase Diguetia canities venom fraction containing DK9.2, DK10, DK11, and DK12. Polyclonal antisera were collected by standard methods (e.g., Antibodies: A Laboratory Manual, E. Harlow and D. Lane, eds., Cold Spring Harbor Laboratory, 1988; incorporated herein by reference), and were cross-reactive with all three major insecticidal D. canities toxins (DK9.2, DK11, DK12). These antisera were used, by standard techniques (Harlow and Lane, ibid.), to quantify the levels of recombinant DK9.2 produced by infecting insects or insect cell lines with vAcDK9.2. Recombinant DK9.2, purified by reversed-phase HPLC and quantified by spectrophotometric methods (i.e., $A_{280}$) as described above, was used as a standard in these immunoassays.

Example 16

Expression of recombinant DK9.2 in insect cells

Three insect cell lines (SF-9 and SF-21, derived from the fall armyworm, and Tn5/BTI-TN-5B1-4, derived from the cabbage looper) were infected with vAcDK9.2 and evaluated for the expression of rDK9.2. Cells were seeded into T-75 flasks at a density of $2\times10^6$ cells/ml, allowed to attach, and then infected with vAcDK9.2 at a MOI of 4. After 1 hour, the remaining free virions were removed by repeated rinsing of the cells and fresh tissue culture medium was added. Samples of the medium were taken over a 112 hour period and evaluated by immunoassay, using the antisera described above. Expression of rDK9.2 in all three cell lines peaked at 72 hours post infection. Peak rDK9.2 expression levels in SF-9, SF-21, and Tn5 cells were 0.9 mg/l, 1.3 mg/l, and 2.0 mg/l, respectively. Combined with the data regarding in vivo expression of rDK9.2, these results clearly indicate the feasibility of producing recombinant Diguetia toxins in a variety of insect cell lines.

TABLE VII

| SEQUENCE ID # | DESCRIPTION |
| --- | --- |
| 1 | Amino acid sequence of DK 9.2 |
| 2 | Coding cDNA sequence of DK 9.2 |
| 3 | Amino acid sequence od DK 11 |
| 4 | Coding cDNA sequence of DK 11 |
| 5 | Amino acid sequence of DK 12 |
| 6 | Complete cDNA sequence encoding DK 9.2 |
| 7 | Amino acid sequence for the signal/leader sequence of precursor DK 9.2 |
| 8 | DNA sequence for the promoter region DK 9.2 |

---

We claim:

1. A recombinant baculovirus expression vector, capable of expressing a DNA sequence encoding an insecticidally effective peptide comprising an amino acid sequence selected from the group consisting of SEQ ID NO:1, SEQ ID NO:3, and SEQ ID NO:5 isolatable from Diguetia spider venom in a eukaryotic or prokaryotic host cell or in a host insect cell.

2. The recombinant baculovirus expression vector according to claim 1 wherein said expression vector is a baculovirus genome comprising said DNA sequence inserted into a polyhedrin gene and under the transcriptional control of a baculovirus polyhedrin promoter.

3. A method of controlling invertebrate pests comprising contacting said pests with a recombinant baculovirus capable of expressing an effective amount of a peptide comprising an amino acid sequence selected from the group consisting of SEQ ID NO:1, SEQ ID NO:3, and SEQ ID NO:5 isolatable from Diguetia spider venom.

4. An insecticidal composition comprising an insecticidally effective amount of a recombinant baculovirus according to claim 3 in an agriculturally or horticulturally acceptable carrier.

5. The recombinant baculovirus expression vector of claim 1, wherein said peptide comprises SEQ ID NO:1.

6. The recombinant baculovirus expression vector of claim 1, wherein said peptide comprises SEQ ID NO:3.

7. The recombinant baculovirus expression vector of claim 1, wherein said peptide comprises SEQ ID NO:5.

8. The recombinant expression vector of claim 1 wherein said DNA sequence comprises SEQ ID NO:2.

9. The recombinant expression vector of claim 1 wherein said DNA sequence comprises SEQ ID NO:4.

10. The recombinant expression vector of claim 1 wherein said DNA sequence comprises SEQ ID NO:6.

* * * * *